(12) United States Patent
Kosugi et al.

(10) Patent No.: US 9,074,200 B2
(45) Date of Patent: Jul. 7, 2015

(54) METHOD FOR RECYCLING ENZYME

(75) Inventors: Akihiko Kosugi, Ibaraki (JP); Rattiya Waeonukul, Ibaraki (JP); Yutaka Mori, Ibaraki (JP)

(73) Assignee: Japan International Research Center for Agricultural Sciences, Ibaraki (JP)

( * ) Notice: Subject to any disclaimer, the term of this patent is extended or adjusted under 35 U.S.C. 154(b) by 299 days.

(21) Appl. No.: 13/137,050

(22) Filed: Jul. 18, 2011

(65) Prior Publication Data

US 2012/0070874 A1    Mar. 22, 2012

(30) Foreign Application Priority Data

Jul. 18, 2010 (JP) ................................. 2010-162362
Mar. 1, 2011 (JP) ................................. 2011-044541

(51) Int. Cl.
| | |
|---|---|
| C12N 9/00 | (2006.01) |
| C12N 9/96 | (2006.01) |
| C12N 1/20 | (2006.01) |
| C12N 15/00 | (2006.01) |
| C07H 21/04 | (2006.01) |
| C12N 9/42 | (2006.01) |
| C12P 19/02 | (2006.01) |
| C12P 19/14 | (2006.01) |

(52) U.S. Cl.
CPC .......... *C12N 9/2434* (2013.01); *C07K 2319/20* (2013.01); *C12P 19/02* (2013.01); *C12P 19/14* (2013.01); *C12P 2203/00* (2013.01)

(58) Field of Classification Search
None
See application file for complete search history.

(56) References Cited

FOREIGN PATENT DOCUMENTS

| | | |
|---|---|---|
| JP | 2007-319040 A | 12/2007 |
| JP | 2010-098951 A | 5/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Eric A Johnson et al.; "Saccharification of Complex Cellulosic Substrates by the Cellulase System from *Clostridium thermocellum*", MIT, vol. 43, No. 5, pp. 1125-1132, Applied and Environmental Microbiology (May 1982).
Alisdair B. Boraston et al., "Carbohydrate-binding modules: fine-tuning polysaccharide recognition", pp. 769-781, Biochemistry and Microbiology University of Victoria et al.; Biochemical Society (2004).
Arnold L. Demain et al., "Cellulase, Clostridia and Ethanol", Charles A. Dana Research Institute for Scientists Emeriti, Drew University et al., vol. 69, No. 1, pp. 124-154, Microbiology and Molecular Biology Reviews (Mar. 2005).
Office Action of Japan Patent Office for application No. 2011-044541 dated May 13, 2014.
M. Tu, et al., "The Potential of Enzyme Recycling During the Hydrolysis of a Mixed Softwood Feedstock", Bioresource Technology 100 (2009), pp. 6407-6415, www.elsevier.com/locate/biortech.
L. P. Ramos, et al., "The Use of Enzyme Recycling and the Influence of Sugar Accumulation on Cellulose Hydrolysis by Trichoderma Cellulases", Enzyme Microb. Technol., 1993, vol. 15, January, pp. 19-25.
E. Morag (Morgenstern), et al., "Affinity Digestion for the Near-Total Recovery of Purified Cellulosome from *Clostridium thermocellum*", Enzyme Microb. Technol., 1992, vol. 14, April, pp. 289-292.
P. Tomme, et al., "Characterization and Affinity Applications of Cellulose-Binding Domains", Journal of Chromatography B, 715 (1998), pp. 283-296.
E. Ong, et al., "Enzyme Immobilization using a Cellulose-Binding Domain: Properties of a B-Glucosidase Fusion Protein", Enyzme Microb. Technol., 1991, vol. 13, January, pp. 59-65.
Z. Liu, et al., "Production, Purification, and Characterization of a Fusion Protein of Carbonic Anhydrase from *Neisseria gonorrhoeae* and Cellulose Binding Domain from *Clostridium thermocellum*", American Institute of Chemical Engineers, 2008, pp. 68-74. www.interscience.wiley.com.
R. Breves, et al., "Genes Encoding Two Different B-Glucosidases of *Thermoanaerobacter brockii* Are Clustered in a Common Operon", Applied and Environmental Microbiology, Oct. 1997, pp. 3902-3910.
A. Kosugi et al. http://togodb.dbcls.jp/yokou_abstract/show/201002948242036.

* cited by examiner

*Primary Examiner* — Christian Fronda
(74) *Attorney, Agent, or Firm* — Fishman Stewart Yamaguchi PLLC

(57) ABSTRACT

In saccharification of cellulose, chimeric β-glucosidase having a region exhibiting thermophilic bacteria-derived β-glucosidase activity and a module combinable to cellulose is used along with cellulosome, and at the completion of saccharification of cellulose, a cellulosic substrate is added to make the chimeric β-glucosidase and cellulosome attach to the cellulosic substrate for separation.

18 Claims, 17 Drawing Sheets

METHOD FOR RECYCLING ENZYME

TECHNICAL FIELD

The present invention relates to a technique of recovering and reusing an enzyme from a solution used for substrate conversion reaction using the enzyme.

BACKGROUND OF THE INVENTION

Cellulosic biomass such as bagasse, rice straws, chaff, waste mushroom beds, compost, and woodchips is attracting attention as energy resources that do not threaten food production and as raw materials for chemical industry. In particular, a technique for efficiently saccharizing fermentation feedstock is much needed to convert cellulosic biomass into fuel ethanol.

However, saccharizing technique applicable to cellulosic biomass is much more complicated than the one applicable to starch because cellulose, a major component of cellulosic biomass, is macromolecular polysaccharide having a firm and persistent crystal structure.

There are three ways of saccharizing cellulosic biomass, namely physical, chemical, and enzymatic saccharification methods.

Physical saccharification includes processes using a ball mill or oscillating mill, and those performing steam explosion or pressurized hot-water treatment. However, since physical treatment requires enormous energy, it is used as pretreatment for chemical and enzymatic saccharification in many cases.

Chemical saccharification uses alkali or acid. Acid saccharification has often been used from long ago. Acid saccharification includes concentrated sulfuric acid saccharification and two-step saccharification using dilute sulfuric acid. Since both methods use sulfuric acid, waste treatment and reduction in environmental load are necessary, and there is a limitation in reducing cost and improving energy conversion efficiency.

Compared with acid saccharification, enzymatic saccharification bears less burden of recovering and treating waste liquid, and cost for building chemical-resistant facilities can be saved. In addition, saccharide yield is high because excess decomposition does not occur, and that is why the method has been in practical use as enzymatic saccharification of biomass high in starch content. However, since cellulose has a complicated crystal structure with crystalline cellulose surrounded by hemicellulose and lignin as described above, enzymatic saccharification of cellulosic biomass is extremely difficult compared with starch biomass. Consequently, pretreatment such as breaking crystal structure by physical or chemical pretreatment is currently performed, or a large amount of hemicellulase or cellulase are used in combination before enzymatic saccharification treatment is performed.

Since hemicellulase and cellulase derived from *Trichoderma reesei*, which is an aerobic filamentous fungus, are used industrially as cellulose diastatic enzymes, study of *Trichoderma* fungi has been conducted vigorously (JP2007-319040A).

It has recently been found that a type of anaerobic microorganism produces cellulosome, an enzymatic complex capable of decomposing cellulose quite efficiently.

Cellulosome has a protein-based structure with a number of macromolecular-polysaccharide-degrading enzymes bonded together. As a result of acting on cellulose in cooperation, these enzymes exhibit extremely high macromolecular-polysaccharide-degrading activity (Mocrobiol Mol Biol Rev. 2005 March; 69 (1); 124-54 and Biochem J. 2004 Sep. 15; 382 (Pt3): 769-81).

SUMMARY OF INVENTION

Technical Problem

It has been pointed out that a large amount of enzymes derived from *Trichoderma reesei* are needed to bring them into practical use because its substrate decomposing speed is slow.

Since the enzyme activity of cellulosome is inhibited by accumulation of cellobiose, a final product of enzyme reaction of macromolecular polysaccharides, saccharification efficiency degrades in the latter period of reaction, which is a problem.

The present invention intends to reduce enzyme usage by recycling enzymes without degrading enzyme activity in saccharification of cellulose.

The present invention also intends to provide enzymes that can be used repeatedly for saccharification of cellulose.

Solution to Problem

Focusing attention on the fact that cellulosome has a cellulose-binding module, the inventors found after earnest study that by allowing an enzyme having cellulosome to be combined with cellulose, the enzyme can be separated from reaction system quite easily, and that the separated enzyme can be used repeatedly without degrading its enzyme activity. The present invention has thus been achieved.

A method for recycling an enzyme, comprising: combining an enzyme having a module combinable with cellulose and a cellulosic substrate, and using the cellulosic substrate-bound enzyme obtained repeatedly.

The enzyme of the present invention is β-glucosidase or chimeric β-glucosidase, which have a region exhibiting β-glucosidase activity and a module combinable with cellulose.

Advantageous Effects of Invention

Since the method of the present invention reduces the amount of the enzyme in an enzyme reaction system to be discharged to outside the reaction system, the enzyme can be separated and recovered efficiently. Consequently, the enzyme need not be added every time it is reused, which reduces enzyme usage as a whole. If there are two or more types of enzymes in the enzyme reaction system, in particular, the enzymes are combined with a cellulosic substrate, and thus separated collectively, which may prevents specific enzyme activity only from being lost.

DESCRIPTION OF EMBODIMENTS

The present invention is hereinafter described in detail by referring to some embodiments and examples.

Embodiment 1

In embodiment 1 is a method for recycling an enzyme, comprising: combining an enzyme having a module combinable with cellulose and a cellulosic substrate, and using the cellulosic substrate-bound enzyme obtained repeatedly.

Figure 1:
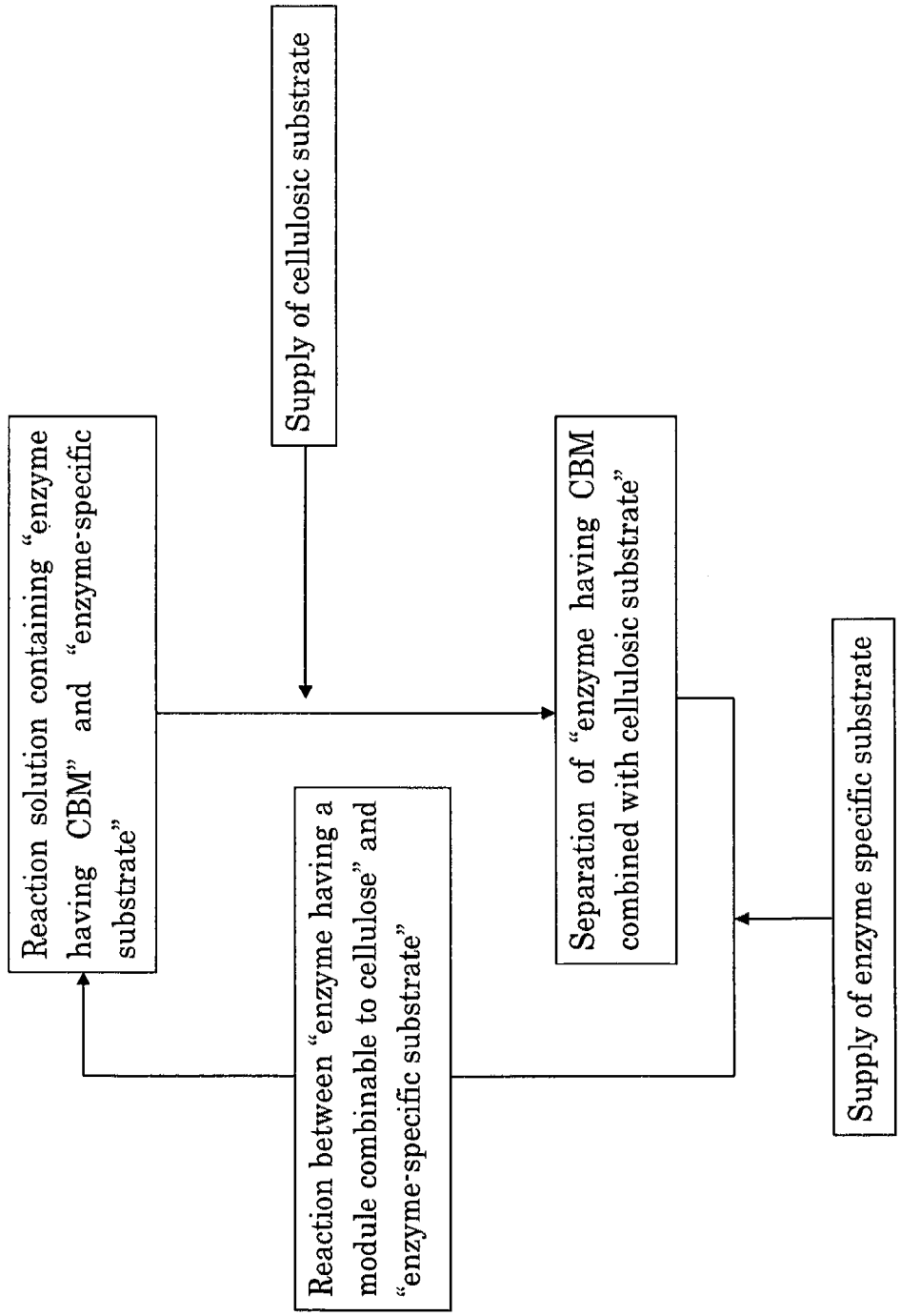
FIG. 1 is a flow chart exhibiting the method of recycling an enzyme in embodiment 1 of the present invention.

More specifically, as shown in FIG. 1, a cellulosic substrate is added to an enzyme reaction liquid containing an enzyme having a module combinable to cellulose (carbohydrate binding module [CBM]) (hereinafter referred to as the enzyme having CBM) and an enzyme-specific substrate, the CBM is made to combine with the cellulosic substrate, a cellulosic substrate-bound enzyme having CBM is separated from the enzyme reaction liquid, the enzyme-specific substrate is added to the separated cellulosic substrate-bound enzyme having CBM, and the above procedure is repeated to recycle the enzyme.

In other words, the method for recycle the enzyme having CBM comprises a first step of combining the enzyme having CBM to the cellulosic substrate by adding the cellulosic substrate to the enzyme reaction liquid containing the enzyme having CBM and the enzyme-specific substrate, a second step of separating the enzyme having CBM from the enzyme reaction liquid, and a third step of causing reaction by adding the enzyme-specific substrate to the enzyme having CBM, and by repeating from the first to the third steps, the enzyme having CBM can be used repeatedly.

The carbohydrate binding module (CBM) means a cellulose-binding module, and refers to polypeptide having an amino-acid sequence biochemically combinable to polysaccharide, cellulose, or hemicellulose via hydrophobic bonding, electrostatic bonding, hydrogen bonding, or via inorganic cation such as calcium or magnesium, as described in Biochem J. 2004 Sep. 15; 382(Pt 3)769-81. Consequently, the enzyme having CBM is defined as the enzyme containing CBM in its amino-acid sequence.

Cellulosome is a cellulase complex known to be produced by bacteria belonging to *Clostridium thermocellum, Clostridium cellulovorans, Clostridium cellulolyticum, Clostridium josui, Clostridium acetobutylicum, Clostridium cellobioparum, Clostridium papyrosolvens, Ruminococcus albus, Ruminococcus flavefaciens, Acetivibrio cellulolyticus, Bacteroides cellulosolvens*, and *Butyrivibrio fibrisolvens* genera. However, it is not known that in glucosidase derived from the above cellulosome-generating bacteria, there exists a region such as CBM to be combined with cellulose.

Namely, the enzyme having CBM is defined as the enzyme containing CBM amino-acid sequence and having various enzyme activities, including chimeric enzyme to which CBM is combined by gene recombination. Enzyme activities are not limited but include various functions such as cellulase, hemicellulase, amylase, and glucosidase activities.

As a typical CBM amino-acid sequence, *Clostridium thermocellum* JK-S14 (NITE BP-627) strain CBM amino-acid sequence is shown in sequence No. 1, but CBM amino-acid sequences are not limited to that one. For example, a CBM classified as carbohydrate-binding module family can be selected from the Carbohydrate-Active enZYmes Database (http://www.cazy.org/) for use. It is preferable to use CBM of family 3, of the module family classification table.

Chimeric enzymes having CBM have at least one of the following activities: cellulase, hemicellulase, amylase, and glucosidase activities. Chimeric enzymes can be obtained by culturing a transfectant containing genes fusing a gene coding for CBM at any part of natural enzyme gene sequence such as C-terminal, N-terminal and central region.

A gene sequence coding for CBM can be obtained from *clostoridium* microorganisms that produce cellulosome such as *Clostridium thermocellum* and *Clostridium cellulovorans* described earlier. The gene sequence coding for CBM amino-acid sequence of *Clostridium thermocellum* JK-S14 (NITE BP-627) strain is shown in sequence No. 2.

Similar to the CBM amid-acid sequence, the gene sequence coding for CBM amino-acid sequence is not limited to the gene sequence shown in sequence No. 2.

An enzyme having CBM combines with a cellulosic substrate supplied to the enzyme reaction system, which means that the enzyme having CBM is fixed to a water-insoluble substance because the cellulosic substrate is insoluble in water. The product of reaction and the enzyme combined with the cellulosic substrate are then separated. Since the enzyme having CBM is fixed to the water-insoluble substance, the enzyme can be recovered efficiently from the enzyme reaction system using a simple means such as solid-liquid separation. By adding a new enzyme-specific substrate to the enzyme having CBM combined with the cellulosic substrate obtained by separation, the enzyme having CBM can be used repeatedly.

Since the cellulosic substrate is decomposed into saccharides in the reaction system in which the enzyme-specific substrate is the same as cellulosic substrate, every time the reaction is completed, the cellulosic substrate is supplied to the enzyme reaction system to combine the enzyme having CBM with the cellulosic substrate. If there is residue in the reaction system, it is desirable that the residue be removed before the cellulosic substrate is supplied.

If the enzyme-specific substrate and the cellulosic substrate are different substances, a cellulose-decomposing enzyme, such as cellulosome or cellulase, may be allowed to exist in the enzyme reaction system in order to promote efficient enzyme reaction. When using the cellulose-decomposing enzyme and the enzyme having CBM in combination, the cellulosic substrate must be supplied to the enzyme reaction system every time the reaction is completed.

In this way, the enzyme having CBM is separated from the enzyme reaction system for reuse, there is no need to add a new enzyme to the enzyme reaction system.

A plurality of enzymes having various activities and modules combinable to cellulose may be allowed to exist in the enzyme reaction system. Namely, by combining a plurality of enzymes existing in the enzyme reaction system with the cellulosic substrate, thus separating them from the enzyme reaction liquid, a plurality of enzymes can be reused.

Embodiment 2

In embodiment 2, this method for recycling enzymes uses two enzymes, namely cellulosome and β-glucosidase having CBM. Embodiment 2 differs from Embodiment 1 in that two types of enzymes, namely cellulosome and β-glucosidase having CBM, are specified as the enzymes having CBM.

It is known that when cellulosic biomass is saccharized by cellulosome, the enzyme activity of cellulosome is inhibited by cellobiose, the final product of the enzyme reaction, and consequently, the cellulosic biomass cannot be decomposed into cellobiose or oligosaccharide efficiently.

In order to remove cellobiose from the enzyme reaction system in the saccharification reaction of cellulosic biomass using cellulosome, the inventors used β-glucosidase in combination. Cellulose-decomposing efficiency improved at first, but after repetitive use, the cellulose-decomposing efficiency was found to decrease, maybe because β-glucosidase, which is derived from thermophilic and anaerobic bacteria, is lost as a result of repetitive reuse.

To suppress the decrease in the enzyme reaction efficiency when cellulosome and β-glucosidase are used in combination, chimeric β-glucosidase, which fuses CBM with the C-terminal or N-terminal of β-glucosidase, was used. As a result, the cellulose-decomposing efficiency was found not to decrease even after repetitive use.

Specifically, the method of this embodiment is characterized in that a cellulosic substrate is added to an enzyme reaction liquid containing a cellulosic substrate, β-glucosidase having CBM, and cellulosome to allow the β-glucosidase having CBM and the cellulosome to be combined with the cellulosic substrate, the β-glucosidase having CBM and the cellulosome combined with the cellulosic substrate are separated from the reaction system, and thus the β-glucosidase having CBM and the cellulosome combined with the cellulosic substrate are used repeatedly.

Figure 2:
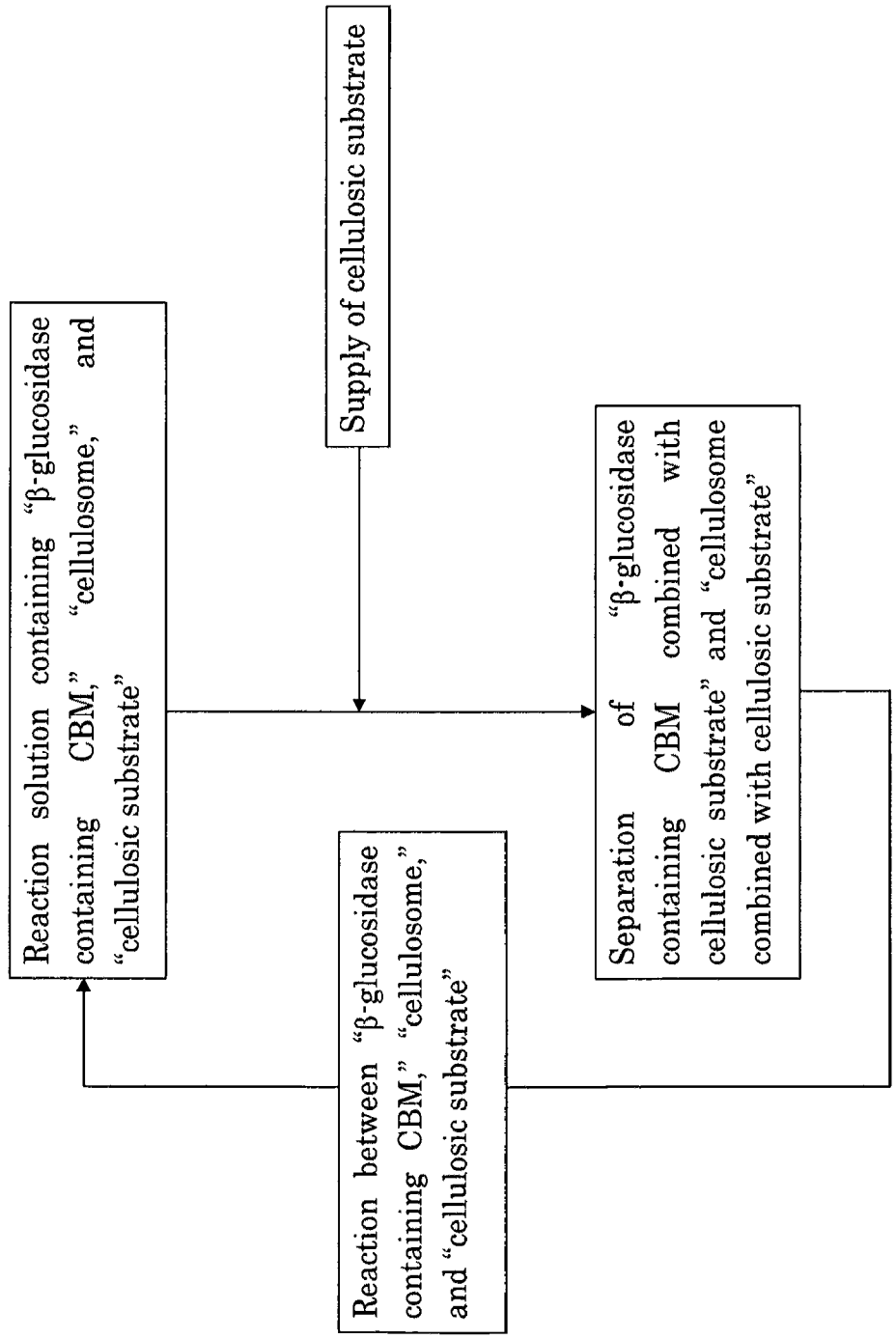
FIG. 2 is a flow chart exhibiting the method of recycling an enzyme in embodiment 2.

FIG. 2 shows the flow of the enzyme recycling method of this embodiment.

Specifically, the enzyme recycling method of this embodiment comprises a first step wherein a cellulosic substrate is added to an enzyme reaction liquid containing a cellulosic substrate, β-glucosidase having CBM, and cellulosome, a second step wherein the β-glucosidase having CBM and the cellulosome are separated, and a third step wherein the cellulosic substrate is added to the separated β-glucosidase having CBM and the cellulosome, and by repeating steps from 1 to 3, the β-glucosidase and the cellulosome can be used repeatedly.

Cellulosome is generated by *Clostridium* bacteria, and the one generated by bacteria classified as *Clostridium thermocellum* and *Clostridium cellulovorans* can be used.

The β-glucosidase used for the present invention is generally defined as an enzyme having an enzyme catalyst capable of converting the cellobiose defined as enzyme commission numbers 3, 2, 1, and 21 (EC3, 2, 1, 21) into two glucose molecules.

The β-glucosidase having CBM is chimeric β-glucosidase fusing CBM. β-glucosidase derived from fungi may be used. However, enzymes derived from thermophilic bacteria are desirable. If β-glucosidase derived from fungi is used, the number of times of reuse is lower than the case in which β-glucosidase derived from thermophilic bacteria is used.

Any β-glucosidase of biological origin can be used, provided that it has reaction conditions comparable to those of cellulosome to be used and that it also has glucosidase activity. For example, when cellulosome derived from *Clostridium thermocellum* is used, it may be made to react with the β-glucosidase having activity within the optimum temperature range of 50° C. to 80° C. and the optimum pH range of 5 to 9.

It is desirable to use β-glucosidase having microbially-derived amino-acid sequences. When cellulosome derived from *Clostridium thermocellum* is used, it is desirable to use thermophilic bacteria-derived β-glucosidase, although the conditions also depend on the reaction conditions of the cellulosome to be used. Specifically, as thermophilic bacteria-derived β-glucosidase, those derived from *Acidothermus, Caldicellulosiruptor, Clostridium, Geobacillus, Thermobifida, Thermoanaerobacter, Thermobispora, Thermodesulfovibrio, Thermomicrobium, Thermomonospora, Thermosipho, Thermotoga, Thermus, Tolumonas, Treponema, Aciduliprofundurn, Caldivirga, Desulfurococcus, Picrophilus, Pyrobaculum, Pyrococcus, Staphylothermus, Sulfolobus, Thermococcus, Thermofilum, Thermoplasma, Thermoproteus,* and *Thermosphaera* may be used. In addition, any bacteria can be used, provided that they produce enzymes classified into families 1, 3, 9, 30, and 116.

As β-glucosidase, in addition to the enzymes listed above, protein classified into 1, 3, 9, 30, and 116 in glycoside hydrolase family classification that appears in the Carbohydrate-Active enZYmes Database (http://www.cazy.org/) can be used.

β-glucosidase that can be used is not limited to those having bacterium-derived amino-acid sequences described above. Those having homology of approximately 60% with bacterium-derived amino-acid sequences, which are known in the field of genetic engineering to be expressed as protein having the same function, can also be used. The amino-acid sequence having the homology of approximately 60% with sequence No. 1 is therefore included in the scope of the present invention.

It is desirable that CBM to be combined with thermophilic bacterium-derived β-glucosidase have the same amino-acid sequence as that of the CBM of cellulosome to be used in combination. The reason for this is that the bonding behavior of the cellulosome and the β-glucosidase to the cellulose becomes identical, which facilitates separating the both enzymes from the reaction system.

In addition to cellulosome and β-glucosidase having a module combinable to cellulose, enzymes having a module combinable to cellulose and various activities may be made to exist in a plurality of enzyme reaction systems.

The enzymes existing in enzyme reaction systems are made to combine with a cellulosic substrate to separate the enzymes combined with the cellulosic substrate from the enzyme reaction liquid. Since the enzymes can be used repetitively without decreasing the saccharification efficiency of the enzymes combined with the cellulosic substrate, recycling of the enzymes is ensured.

Regarding cellulosome, which is an anaerobic bacterium-derived enzyme, it is known that a reducing agent such as dithiothreitol (DTT) and 2-mercaptoethanol is made to exist in the reaction system (Johnson E A, Sakajoh M, Halliwell G, Media A, Demain A L (1982) Saccharification of complex cellulosic substrates by the cellulase from *Clostridium thermocellum*. Appl. Environ. Microbiol 43: 1125-1132). With the method of this embodiment, a reducing agent may be used to react the cellulosic substrate to both cellulosome and β-glucosidase having the CBM. In this case, however, the saccharification efficiency may decrease through the repetitive use of the enzymes. It is therefore desirable not to allow a reducing agent to exist in the reaction system.

Embodiment 3

Embodiment 3 differs from embodiment 2 in that the cellulosic substrate is a cellulosic biomass containing lignin.

Specifically, the method of this embodiment is characterized in that cellulosic biomass containing lignin is added to an enzyme reaction liquid, which contains cellulosic biomass containing lignin, β-glucosidase having CBM and cellulosome, to allow the β-glucosidase having CBM and cellulosome to combine and react with the cellulosic biomass containing lignin, the β-glucosidase having CBM and cellulosome combined with the cellulosic biomass are separated from the reaction system, and thus the β-glucosidase having CBM and cellulosome combined with the cellulosic biomass are used repetitively.

In other words, the method of recycling enzymes in this embodiment comprises a first step wherein cellulosic biomass containing lignin is added to an enzyme reaction liquid containing cellulosic biomass, β-glucosidase having CBM, and cellulosome to allow the cellulosome and the β-glucosidase having CBM to combine and react with the cellulosic biomass containing lignin, a second step wherein the β-glucosidase having CBM and the cellulosome combined with the cellulosic biomass containing lignin are separated from the reaction system, and a third step wherein cellulosic biomass containing lignin is added to the separated β-glucosidase having CBM and the cellulosome to cause reaction, and by repeating steps from 1 to 3, the β-glucosidase and the cellulosome are used repeatedly.

In this case, it is preferable that the cellulosic biomass containing lignin be immersed in ammonia in advance as pretreatment, and furthermore, blocking treatment be performed after the ammonia-immersion treatment, using one or more types of blocking agents selected from protein, polyethylene glycol, and surface active agents. Blocking treatment is coating the region of lignocellulosic biomass insoluble in acid, by immersing cellulosic biomass having undergone ammonia-immersion treatment in a blocking agent. As blocking agents, skim milk and casein are desirable as protein, and non-ionic surface active agents typified by Tween 20 and Tween 80 are desirable as surface active agents. By blocking treatment, it is considered that non-specific adsorption reaction between protein and reaction group in plant cell walls, such as lignin/lignin-hemicellulose complex, lignin-mineral complex, hydrophobic group other than cellulose and hemicellulose, is suppressed.

With this embodiment, a reducing agent may be used for the first and the third steps wherein cellulosome and β-glucosidase having CBM are made to combine with the cellulosic substrate, but in this case, repetitive use of enzymes may decrease saccharification efficiency. Consequently, it is preferable not to allow a reducing agent to exist in the reaction system.

It is desirable to remove residue of enzyme reaction before adding cellulosic biomass containing lignin to the enzyme reaction liquid of cellulosic biomass containing lignin, β-glucosidase having CBM, and cellulosome. By removing the residue, the number of times of reuse can be increased.

Embodiment 4

In embodiment 4, enzymes having a module combinable to cellulose are made to combine and/or react with a cellulosic substrate in the presence of one or more types of blocking agents selected from protein, polyethylene glycol and surface-active agents to reuse the enzymes.

It is preferable that the blocking agent exists in the reaction system for the enzyme having the module combinable to cellulose and the cellulosic substrate. Also, it is desirable that the enzyme having the module combinable to cellulose be made to contact with the blocking agent before the enzyme reacts with the cellulosic substrate. The contact is allowed if the blocking agent is added to a solution containing the enzymes having the module combinable to cellulose.

Specifically, the method comprises a first step wherein the cellulosic substrate is added after the blocking agent is added to the solution containing the enzymes having the module combinable to cellulose to allow the enzymes having CBM to combine with the cellulosic substrate, a second step wherein the enzymes having CBM are separated from the enzyme reaction liquid, and a third step wherein the enzyme-specific substrate is added to the separated enzymes having CBM to cause reaction, and by repeating steps from 1 to 3, the enzyme having CBM is used repeatedly.

If cellulosome and β-glucosidase having CBM are used as the enzymes having a module combinable to cellulose, and cellulosic biomass containing lignin is used as the cellulosic substrate and/or the substrate specific to the enzyme having CBM, a reducing agent may be allowed to exist in the reaction system. In this case, however, repetitive use of the enzyme may decrease the saccharification efficiency. It is therefore preferable not to allow a reducing agent to exist in the reaction system.

In this case, it is preferable that the cellulosic substrate containing lignin be added after the blocking agent is added to the solution containing cellulosome and β-glucosidase having CBM to allow the enzymes and the substrate to combine and/or react with each other.

The present invention will hereinafter be described in detail by referring to examples. Note that the present invention is not limited to the examples described below.

Example 1

As described previously, the enzyme reaction of cellulosome is inhibited by cellobiose, the final product of the enzyme reaction. In order to exert the saccharifying capability of the cellulosome fully, it is necessary to remove cellobiose from the reaction system. β-glucosidase, an enzyme capable of decomposing cellobiose into glucose, was made to exist with the cellulosome, and the decomposing capability of microcrystal cellulose (sigma cell type 20) was measured.

The following two enzymes were prepared as β-glucosidase:
(1) Commercially available *Aspergillus niger*-derived enzyme (Sigma-Aldrich Co.)
(2) Recombinant β-glucosidase (CgIT) based on the β-glucosidase of *thermoanaerobactor brockii* ATCC33075 (American-type culture collection)

[Preparation of CgIT]

Genomic DNA from *thermoanaerobactor brockii* was extracted according to the following procedure: After *thermoanaerobactor brockii* was cultured using BM7CO-CB liquid culture medium containing cellobiose in concentration of 0.5%, centrifugal separation was conducted at 4° C. and at 10,000 rpm for 5 minutes to recover the microorganism. For bacteriolysis of obtained microorganism, 10% sodium lauryl sulfate (SDS) was added so that the final SDS concentration became 0.5%, proteinase K (1 mg/mL) was also added so that the proteinase K concentration became 5 μg/mL, and kept at 37° C. for an hour for reaction. Furthermore, 10% cetyltrimethylammonium bromide-0.7M sodium chloride solution was added so that the concentration became 1%, and kept at 65° C. for 10 minutes for reaction, the equivalent amount of chloroform-isoamyl alcohol solution was added and mixed thoroughly, and then a water solution was obtained by centrifugal separation performed at 15,000 rpm for 5 minutes.

To this water solution, the equivalent amount of phenol-chloroform-isoamyl alcohol solution was added, and after mixing, centrifugal separation was performed again at 15,000 rpm for 5 minutes to obtain another water solution. Isopropanol of 0.6 times the volume of the obtained water solution was then added to the water solution to allow genomic DNA to be deposited, and by centrifugal separation again, the genomic DNA was prepared. The genomic DNA was washed with 70% Ethanol and dried.

The BM7CO-CB culture medium was prepared at the composition of potassium dihydrogen phosphate of 1.5 g/L, dipotassium hydrogen phosphate of 2.9 g/L, urea of 2.1 g/L, yeast extract of 6.0 g/L, sodium carbonate of 4 g/L, cysteine hydrochloride of 0.05 g/L, and mineral solution of 0.2 mL ($MgCl_2.6H_2O$ of 5 g, $CaCl_2.2H_2O$ of 0.75 g, and $FeSO_4.6H_2O$ of 0.0063 g were dissolved in water of 4 mL). Furthermore, cellobiose was added to the culture medium as a source of carbon in concentration of 5 g/L. The pH of the final culture medium was adjusted to around 7.0.

Using the prepared genomic DNA, oligonucleotide primer CgITF (sequence No. 3: 5'-CGCGGATCCG-GCAAAATTTCCAAGAGAT-3') and CgITR (sequence No. 4: 5'-ATTGCTCAGCATCTTCGATACCATCATC-3') were designed and synthesized, and double-strand amplified DNA sequence having the base pair of approximately 1.4 k was obtained by PCR as CgIT. The amplified CgIT gene sequence is shown in sequence No. 5.

In order to insert the designed oligonucleotide primers CgITF and CgITR into a *E. coli* expression vector, restriction enzyme sites BamHI and Bpu1102 were added. The gene sequence of β-glucosidase-CgIT of *thermoanaerobactor brockii* ATCC33075 can be obtained on the website of the National Center for Biotechnology Information (http://www.Ncbi.nlm.nih.gov/) (GenBank accession No.: CAA91220.1).

By PCR, 16srRNA gene was amplified using ExTaq DNA polymerase (TAKARA BIO INC.) Amplification was performed for one minute at 98° C., one minute at 55° C., and two minutes at 72° C. (one cycle), and the cycle was repeated 30 times (30 cycles).

The amplified band of the PCR product was checked by 0.8% agarose gel electrophoresis, and then the product was purified using Quiagen PCR purification kit (QUIAGEN). The purified PCT product was subjected to restriction enzyme treatment overnight at 37° C. using BamHI (TAKARA BIO INC.) and Bpu1102 (TAKARA BIO INC.).

The PCR product having undergone restriction enzyme treatment was again separated from the product of restriction enzyme decomposition by 0.8% agarose gel electrophoresis to cut off the desired band from the gel, and the band was purified using a gel extraction kit (QUIAGEN).

In order to express CgIT gene in *E. Coli*, pET19b expression vector (MERCK) was also used. This vector is designed to allow 6-residue histidine tag to be connected to the N-terminal of the protein intended for expression. The pET19b expression vector was also subjected to restriction enzyme treatment overnight at 37° C. using BamHI and Bpu1102. After the restriction enzyme treatment, to dephosphorylate the restriction enzyme cutting site, treatment was performed for one hour at 50° C. using alkaline phosphatase (TAKARA BIO INC.) After deactivation of alkaline phosphatase by repeating phenol chloroform extraction, ethanol precipitation treatment was conducted and pET19b expression vector having undergone restriction enzyme treatment was recovered.

To obtain CgIT expression vector, the CgIT gene and pET19b expression vector having undergone the restriction enzyme treatment described above were incubated overnight at 16° C. using T4 ligase (TAKARA BIO INC.) to combine them. *E. Coli* JM109 was transformed using the expression vector CgIT-pET19, and then cultured overnight at 37° C. using Luria-Bertani culture medium (LB culture medium) containing 50 μg/mL ampicillin sodium and 1.5% agar.

The composition of the LB culture medium was as follows: 1 g/L bacto-peptone, 1 g/L sodium chloride, 1 g/L yeast extract, and the final pH of the culture medium was adjusted to around 7.0.

A clone having CgIT-pET19, the desired expression vector, was selected from the grown colony by the following procedure: Expression vector CgIT-pET19 was selected from a *E. Coli* clone using a plasmid extraction kit (QIAGEN), and then DNA sequence was analyzed using BigDye (registered trademark) Terminator v3.1 (Applied Biosystems), PRISM (registered trademark) 3100 Genetic Analyzer (Applied Biosystems), PRISM (registered trademark) 3100 Genetic Analyzer (Applied Biosystems), or PRISM (registered trademark) 3700 DNA Anayzer (Applied Biosystems) using the above primer.

To check whether the gene sequence is correct, homology search was conducted using the website of the National Center for Biotechnology Information (NCBI), and the accuracy was confirmed. To produce a large quantity of CgIT protein, *E. Coli* BL21 (MERCK) was transformed using CgIT-pET19 having the accurate gene sequence, and a *E. Coli* clone allowing high-level protein expression was obtained.

To obtain CgIT, transformed *E. Coli* BL21 having expression vector CgIT-pET19 was cultured for 4 hours at 37° C. in an LB culture medium containing ampicillin sodium, and then isopropyl-D-thiogalactopyranoside in 1 mM concentration was added and culture was continued for 12 hours.

The transformed *E. Coli* BL21 (DE3) having CgIT-pET19 was recovered by centrifugal separation (8,000 rpm, 4° C., 10 min.) The recovered *E. coli* was frozen overnight at −80° C., then suspended in a bacteriolysis buffer solution (50 mM phosphoric acid buffer solution, 300 mM sodium chloride, 10 mM imidazole, pH: 8.0), and then crashed in ice water using an ultrasonic. The obtained turbid solution was subjected to centrifugal separation to separate clear lysis solution and precipitation contained uncrashed transformed *E. coli*, and then the lysis solution only was recovered and filtered using a 0.45 μm filter.

The lysis solution was put to nickel agarose gel column (Ni-NTA agarose gel, QIAGEN) to obtain histidine-tagged CgIT. Further the eluted CgIT was purified through a demineralization column (Bio-Rad Laboratories Inc.) The amount of protein in the histidine-tagged CgIT was measured, after diluting the CgIT with distilled water as required, using BCA protein measurement kit (Thermo Fisher Scientific K.K.). The analytical curve for protein was created using bovine serum albumin.

The amino-acid sequence of CgIT is shown in sequence No. 6.

[Manufacture of Cellulosome]

*Clostridium thermocellum* JK-S14 strain (NITE BP-627) was cultured at 60° C. for 6 days using BM7CO-CL culture medium, which was created by changing the source of carbon of the above-mentioned BM7CO-CB culture medium from cellobiose to 10 g/L microcrystal cellulose.

After the culture, microorganism was removed by centrifugal separation. Amorphous cellulose (phosphoric acid-swollen cellulose) was then added to the culture solution, which was agitated overnight at 4° C. to allow cellulosome to attach to amorphous cellulose. After the agitation, amorphous cellulose was recovered and suspended in 100 mM sodium acetate buffer solution containing 5 mM calcium chloride, the solution was then poured into a dialysis tube (10 kDa cut, Spectra Co-op), and dialysis was performed at 60° C. for approximately 6 hours using distilled water, which was replaced hourly with new distilled water.

By this reaction, cellobiose and cello-oligosaccharide, the byproduct of the reaction of amorphous cellulose decomposed by cellulosome, are diffused into the distilled water by dialysis, and thus decomposed thoroughly without being subjected to reaction inhibition. As a result, cellulosome only can be recovered easily from the dialysis tube.

The obtained dialyzate solution was used for subsequent experiments as a cellulosome enzyme fraction. After the cellulosome was diluted with distilled water to appropriate concentration, using the BCA protein measuring kit similar to the above, the amount of protein in the cellulosome was measured.

The activity (unit) of β-glucosidase was calculated by measuring the amount of p-nitrophenol, which is liberated by enzyme reaction with p-nitrophenol galactopyranoside used as a substrate described in "Wood, W A., Kellog, S. T., 1988. Methods in Enzymology. 160, New York: Academic Press." The amount generating 1 μmol p-nitrophenol per minute was defined as enzyme activity of one unit (U).

Cellulosome of 0.5 mg and β-glucosidase were added to a sodium acetate buffer solution of 100 mM (pH 6.0) containing 1% sigma cell type 20 and 5 mM calcium chloride. Cellulose decomposition rate was measured by sampling at given intervals, and by measuring generated cellobiose and glucose with a high-performance liquid chromatograph (Shimadzu Corporation, Prominence) using a differential refractive index detector, Aminex HPX-87P column (Bio-Rad Laboratories Inc.)

As the first saccharide concentration, 72 wt % sulfuric acid of 3 mL was added to sigma cell type 20 of 0.3 g, the mixture was agitated thoroughly, and then subjected to hydrolytic degradation for one hour. Distilled water of 80 mL was added to the mixture, which was then subjected to autoclave treatment at 121° C. for one hour, and filtered using a glass filter to obtain filtrate. The filtrate was placed in a strong anion column, and then a part of the filtrate was measured with the above high-performance liquid chromatograph (Shimadzu Corporation, Prominence) using a differential refractive index detector, Aminex HPX-87P column (Bio-Rad Laboratories Inc.) Based on the weight of cellulose used, the amount of glucose measured was converted into the amount of total sugar, which was regarded as 100%.

Figure 3:
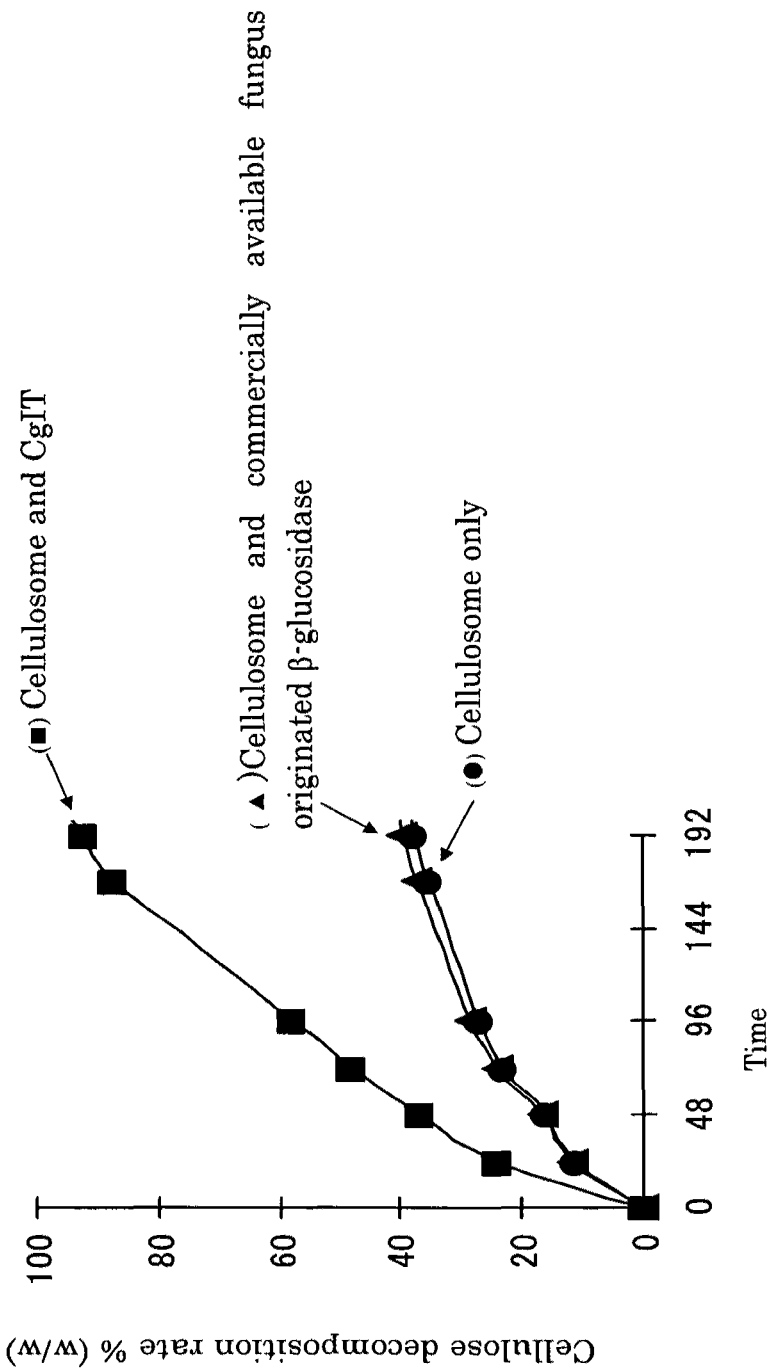
FIG. 3 is a chart illustrating the effect of combined use of cellulosome derived from *Clostridium thermocellum* JK-S14 and β-glucosidase (CgIT) derived from *thermoanaerobactor brockii* ATCC3307 on the Avicel degrading ability.

FIG. 3 illustrates microcrystal cellulose decomposition rate (%: w/w) obtained when cellulosome only was used and when cellulosome and β-glucosidase were used in combination. The black circles in the figure represent the decomposition reaction of cellulosome only, the black triangles represent that of cellulosome and commercially available *Aspergillus niger* β-glucosidase (0.5 mg; 0.93 U) used in combination, and the black squares represent that of cellulosome and CgIT (0.01 mg; 0.24 U).

The cellulose-degrading capability of cellulosome only and that of cellulosome and commercially available *Aspergillus niger* β-glucosidase used in combination were both as low as approximately 40%, exhibiting almost no effect and indicating that the capability of cellulosome was inhibited by cellobiose. It was also found that the combined use of cellulosome and commercially available *Aspergillus niger* β-glucosidase was mostly ineffective. Meanwhile, the combined use of cellulosome and CgIT resulted in mostly perfect degradation. Specifically, the cellobiose generated by cellulosome was effectively degraded into glucose, and thereby undisturbed by product inhibition.

It was thus found that the combined use of cellulosome and *thermoanaerobactor brockii* ATCC33075 β-glucosidase CgIT has much higher cellulose decomposition rate than the combined use of cellulosome and commercially available *Aspergillus niger* β-glucosidase.

Example 2

Since the skeletal protein (CipA) of cellulosome has a cellulose-binding module, the entire cellulosome can be attached to cellulose. Meanwhile, β-glucosidase does not have a module combinable to carbohydrates. Consequently, to recycle cellulosome, β-glucosidase must be added continuously.

Figure 4:
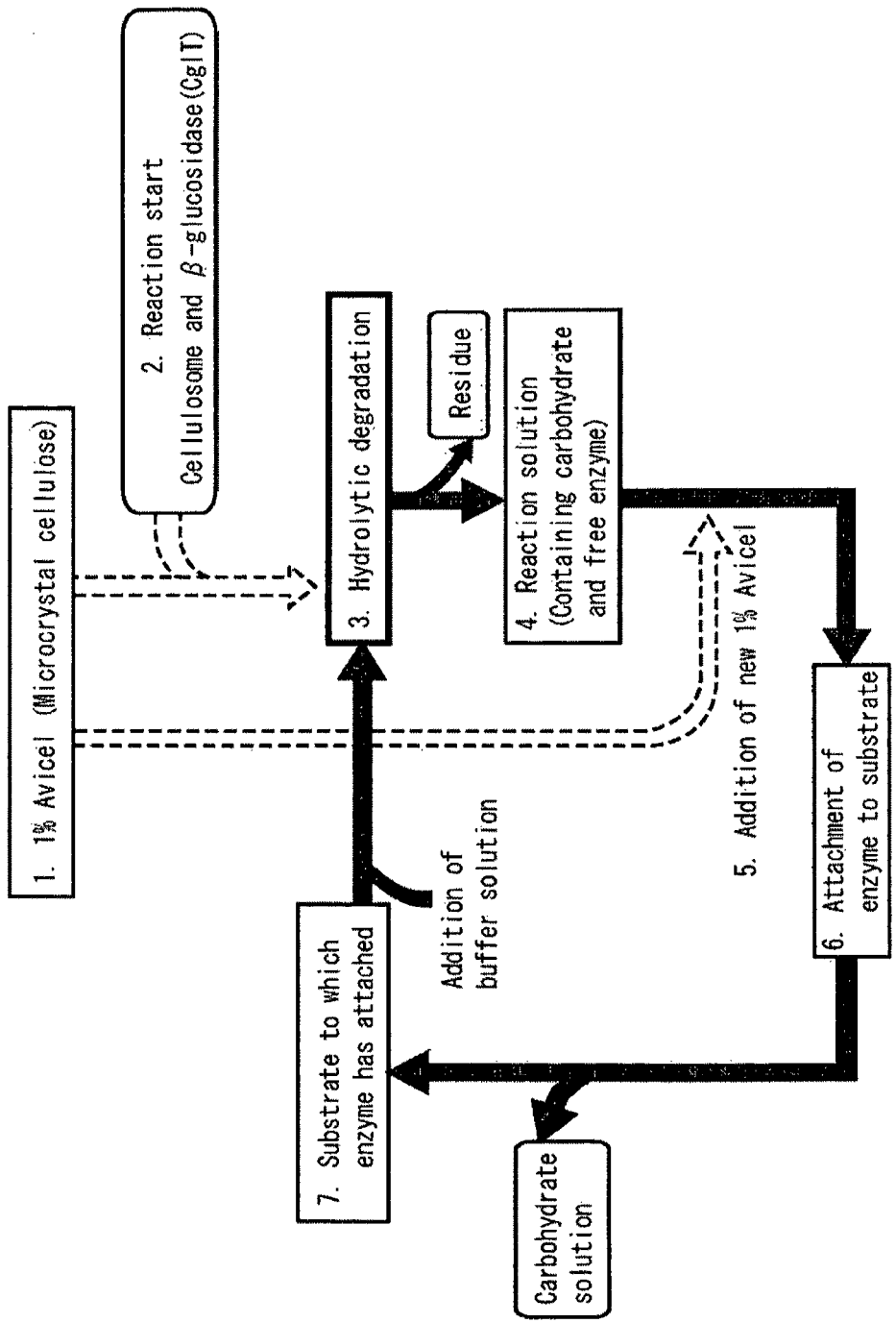
FIG. 4 illustrates a recycling saccharification process of Avicel based on a combined use of cellulosome and CgIT.

To check whether β-glucosidase can be recycled, microcrystal cellulose (Avicel) was used in recycling reaction of cellulosome and CgIT. FIG. 4 illustrates the procedure of the recycling reaction.

Specifically, cellulosome and β-glucosidase were made to react with Avicel (microcrystal cellulose), and after Avicel was subjected to hydrolytic degradation, Avicel was added again to the reaction solution, and the enzyme attached to Avicel was separated for reuse.

Using 1% Avicel, 2 mg cellulosome, and 0.5 mg CgIT (5 U), which function as substrate, recycling saccharification reaction was started at 60° C. in a 100 mM acetic acid buffer solution containing 5 mM calcium chloride.

After 24-hour enzyme hydrolytic degradation, residue was removed, Avicel cellulosic substrate was added to the reaction solution in the same amount and concentration as the initial substrate, and the enzyme was made to attach to the substrate at 4° C. for 6 hours. A buffer solution was then added, and enzyme hydrolytic degradation reaction was started again. Enzymes such as cellulosome and CgIT were not added in the reaction of the second and subsequent rounds to see whether the enzyme initially added was reusable.

Figure 5:
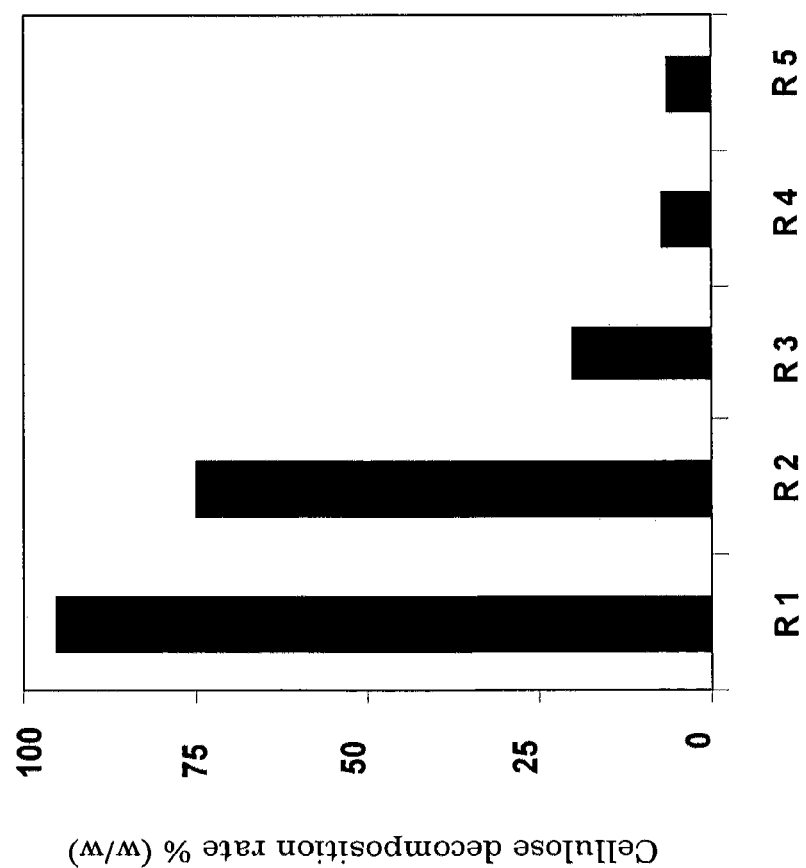
FIG. 5 is a chart showing Avicel degrading ability by round of recycling saccharification reaction based on combined use of cellulosme and CgIT.

FIG. 5 shows the result obtained. The cellulose decomposition rate of the first round was as high as 94% and that of the second round was still as high as 75%. However, the decomposition rate declined rapidly in the third and subsequent rounds, with that of the fifth round found as low as 6%.

The result indicates that CgIT flows out of the reaction system through the repetitive saccharification cycles of recycling saccharification, meaning that the amount of enzyme necessary to maintain high cellulose decomposition rate is insufficient. It was found that the behavior of cellulosome and that of CgIT during reaction must be coincided in order to perform recycling saccharification while maintaining high cellulose decomposition rate.

Example 3

To match the behavior of CgIT to that of cellulosome, it seemed necessary to allow CgIT to have a part of characteristics of the cellulosome structure. It was expected that by allowing CgIT to have CBM of CipA, matching behavior could be obtained. However, β-glucosidase has a protein structure of catalyst domain only in most of the cases, and CgIT does not have cellulose-binding region. Therefore, CgIT fusing CBM owned by structural protein CipA was created.

As described previously, gene sequence coding for CBM amino-acid sequence of *Clostridium thermocellum* JK-S14 (NITE BP-627) strain is shown in sequence No. 2.

In designing CgIT fusing CBM, a type of fusing CBM at N-terminal (CBM-CgIT) and a type of fusing CBM at C-terminal (CgIT-CBM) were created.

In creating CBM-CgIT, oligonucleotide primer CBMF1 (shown in sequence No. 7: 5'-CGCGGATCCGGTTG-GCAATGCAACACCG-3') and CBMFusionN (shown in sequence No. 8: 5'-ACGAAATCTCTTGGAAATTTTG-CATTCGGATCATCTGACGGCGG-3') were used to amplify CBM.

Oligonucleotide primer CBMF1 was designed to have a BamHI restriction enzyme site, and CBMFusionN was designed to include a part of N-terminal amino-acid sequence of CgIT.

CBM gene fragment was amplified by PCR, with genomic DNA used as genetic template of *Clostridium thermocellum* JK-S 14 strain (NITE BP-627), under the same conditions as example 3.

To create CgIT, primer CgITFusion (N) (shown in sequence No. 9: 5'-CCGCCGTCAGATGATCCGAATG-CAAAATTTCCAAGAGATTTCGTT-3') and CgITR (shown in sequence No. 4) described in example 1 were used.

Primer CgITDFusion (N) was designed with a part of the CBM on the C-terminal overlapped. Using the amplified CBM gene (including the gene coding for the CgIT N-terminal amino-acid sequence on 3' side) and CgIT gene (including the gene coding for the CBM C-terminal amino-acid sequence on 5' side) were used as genetic templates, and PCR condition is the same conditions as example 1, using oligonucleotide primer CBMF1 and CgITR.

By PCR, a DNA fragment of approximately 1.9 kb of being fused CBM and CgIT was obtained.

In creating CgIT-CBM of the type fusing CBM on C-terminal, oligonucleotide primer CgITF (shown in sequence No. 3) described in example 1 and CgITR-Fusion (C) (shown in sequence No. 10: 5'-CGGTGTTGCATTGCCAACATCTTC-GATACCATCATC-3') were used to amplify the CgIT gene.

The oligonucleotide primer CgITR-Fusion (C) was designed with a part of the N-terminal of the CBM overlapped.

To amplify the CBM gene to the C-terminal, oligonucleotide primer CBM3F-Fusion (C) (shown in sequence No. 11: 5'-GATGATGGTATCGAAGATGTTGGCAATG-CAACACCG-3') and oligonucleotide primer CBM3R (shown in sequence No. 12: 5'-ATTGCTCAGCATTCGGAT-CATCTGACGGCGGTAT-3') were used.

Oligonucleotide primer-CBM3F-Fusion (C) was designed with a part of the gene coding for the amino-acid sequence on the C-terminal of CgIT overlapped.

Oligonucleotide primer-CBM3R was designed so that the cutting site of restriction enzyme Bpu1102 was to be imparted.

Using the amplified CgIT gene (including the gene coding for the amino-acid sequence at C-terminal of CBM on 3' side) and CBM gene (including the gene coding for the amino-acid sequence at N-terminal of CgIT on 5' side) were used as genetic templates, PCR condition is the same conditions as example 1.

As a result of PCR, a DNA fragment of approximately 2 kb, which can be obtained when CgIT and CBM are fused, was obtained.

Two fusion genes obtained by PCR were cut using restriction enzymes, BamHI and Bpu1102, purified, and inserted between BamHI and Bpu1102 restriction enzyme sites of pET19b to create CgIT expression plasmid fusing CBM. The two expression plasmids were introduced to *E. Coli* BL21 respectively, and expression strains were obtained.

The gene sequence of CBM-CgIT fusing CBM on the N-terminal is shown in sequence No. 13, and the gene sequence of CgIT-CBM fusing CBM on the C-terminal is shown in sequence No. 14.

To check general characteristics of β-glucosidase fusing CBM, recombinant protein was expressed for each and purified. Since both of the purified proteins had a histidine-tagged structure, purification was continued, as in the case of recombinant CgIT described above, until a single band is obtained in a nickel agarose column by SDS-PAGE.

To measure the cellulose-binding capability of purified CBM-fusing β-glucosidase, its binding capability was tested using cellulose. To examine the cellulose-binding capability, purified protein of 0.2 mg was mixed in a 50 mM sodium acetate buffer solution (pH6.0) containing 10 g Avicel and left as it was overnight at 4° C. Centrifugal separation was then performed to separate supernatant from deposit (namely cellulose), and the separated cellulose was washed three times in 50 mM sodium acetate buffer solution (pH 6.0). Centrifugal separation was performed again to recover the deposit, which was then suspended in 50 mM sodium acetate buffer solution (pH 6.0) and used for SDS-PAGE.

Comparison with CgIT revealed the following: A band identical to that of purified protein was found in the deposit fraction both with CBM-CgIT and CgIT-CBM, whereas in the case of CgIT it was found both in supernatant and the fraction washed with the buffer solution. It is therefore determined that the used CBM gene had cellulose-binding capability, and that it was functioning within CgIT.

In addition, to check whether β-glucosidase activity had changed, the β-glucosidase activity of CgIT, CBM-CgIT, and CgIT-CBM was measured by the method described in example 1. Table 1 summarizes the results obtained.

TABLE 1

| recombinant protein | β-glucosidase activity Specific activity (U/mg protein) | Cellulose-binding capability |
|---|---|---|
| CgIT | 25.0 | Without |
| CBM-CgIT | 4.0 | With |
| CgIT-CBM | 2.0 | With |

CgIT exhibited activity as high as 25 U/mg protein, whereas CBM-fusing type CgIT exhibited drastic decline of β-glucosidase activity, with CBM-CgIT exhibiting 4.0 U/mg protein, and CgIT-CBM exhibiting 2.0 U/mg protein.

The conformational change resulting from fusing CBM is considered to have affected the enzyme catalytic portion.

To check the effect of using CBM-CgIT or CgIT-CBM along with cellulosome on decrease in β-glucosidase activity, cellulose decomposition rate was measured.

Figure 6:
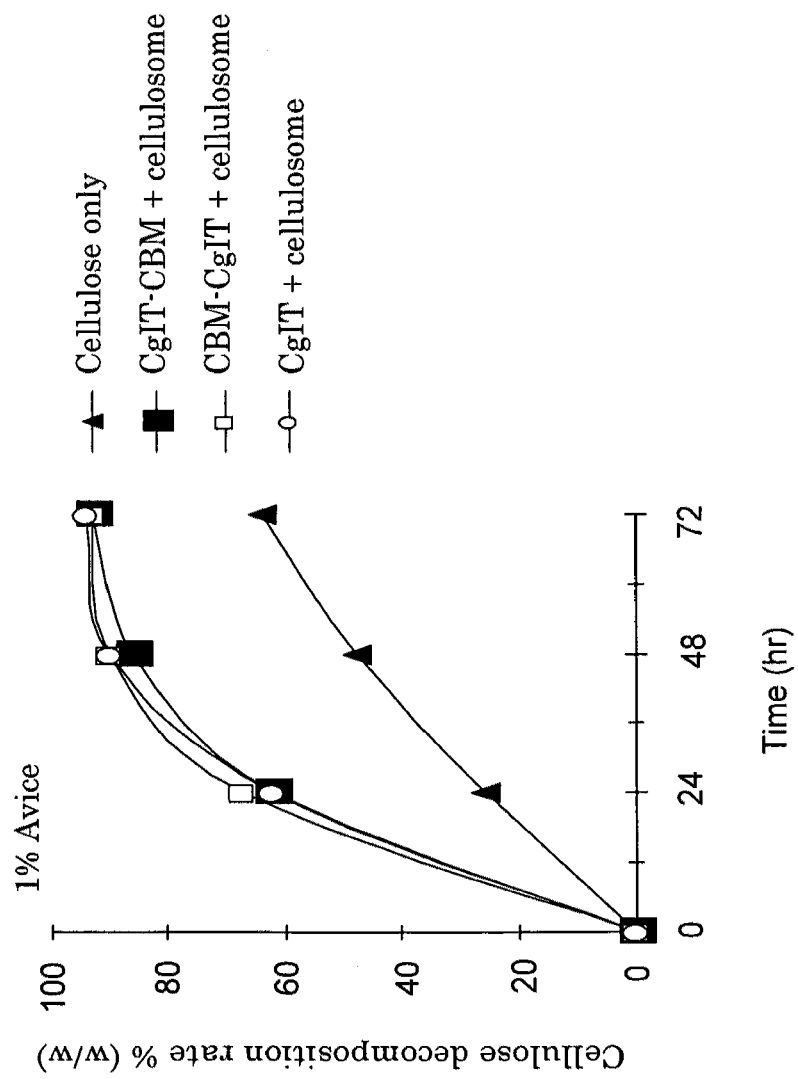
FIG. 6 is a chart showing the effect of combined use of chimeric β-glucosidase fusing cellulose-binding modules (CBM-CgIT and CgIT-CBM) and cellulosome on Avicel degrading ability.

As reaction conditions, 1% Avicel was used, and using the buffer solution and conditions described above, measurement was performed. The obtained results are shown in FIG. 6.

The black triangles in the figure represent the reaction using cellulosome only, white circles represent the reaction using cellulosome and CgIT in combination, white squares represent the reaction using cellulosome and CBM-CgIT in combination, and black squares represent the reaction using cellulosome and CgIT-CBM in combination.

When cellulosome only was used, cellulose decomposition rate as low as approximately 60% was obtained after 72 hours, which means that reaction inhibition was occurring due to accumulation of cellobiose.

When cellulosome and CgIT were used in combination, inhibition did not occur and mostly 100% cellulose decomposition rate was obtained. Meanwhile, with CBM-fusing CgIT, cellulose decomposition rate obtained when cellulose only was used, or slightly higher effect, was expected, considering the decrease in β-glucosidase activity shown above. Surprisingly, however, mostly 100% cellulose decomposition rate was obtained as in the case of CgIT.

These results exhibits that the activity can be recovered in existence of cellulose because of the function of CBM, although the activity cannot be exhibited well by p-nitrophenol glucopyranoside, which is generally used as β-glucosidase substrate. Consequently, the demerit of fusing CBM and CgIT is limited to the decrease in activity when artificial substrate is used.

Since there is no difference in cellulose decomposition rate if CBM-fusing CgIT on the N-terminal or on the C-terminal is used in combination with cellulosome, CBM-CgIT is to be used in the subsequent examples.

Example 4

In order to check whether the behavior of CBM-CgIT and that of cellulosome can be coincided, recycling saccharification reaction was performed according to FIG. 4.

Figure 7:
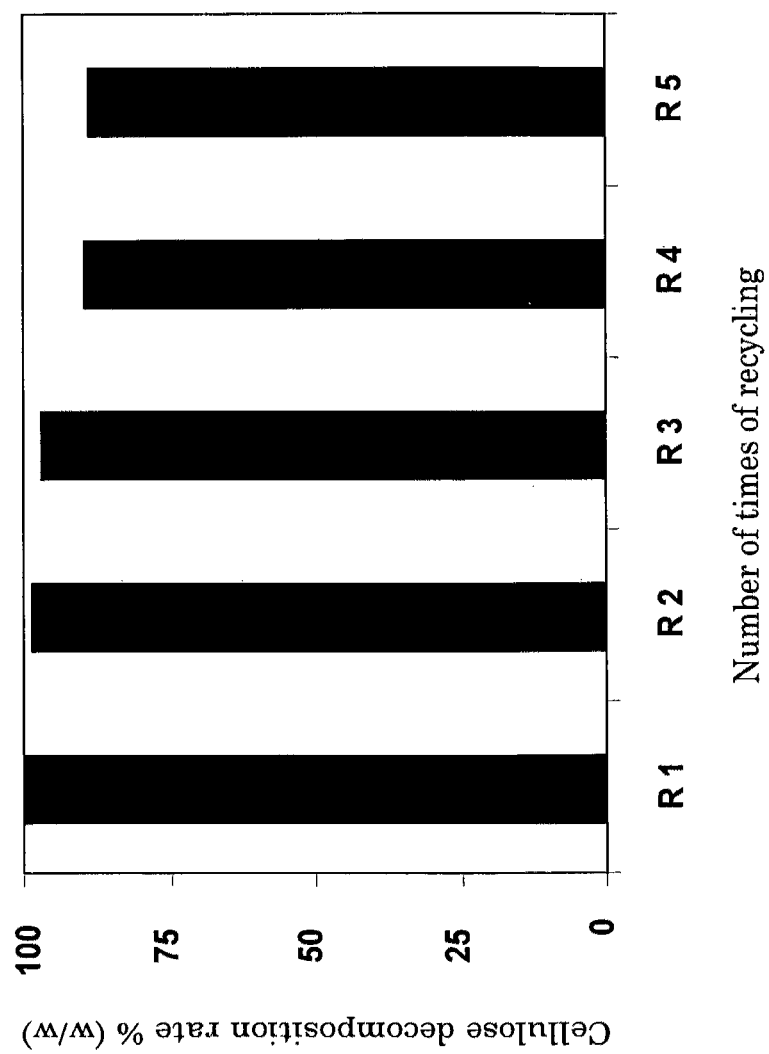
FIG. 7 is a chart showing Avicel degrading efficiency by round of recycling saccharification reaction based on combined use of cellulosome and CBM-CgIT.

The conditions were the same as example 2, namely using 1% sigma cell, 2 mg cellulosome, and 0.5 mg CBM-CgIT (0.8 U), recycling saccharification reaction was started in a 100 mM acetic acid buffer solution (pH 6.0) at 60° C. FIG. 7 shows the results obtained.

It was found that by using cellulosome and CBM-CgIT in combination, they can be used repeatedly at least five times while maintaining the cellulose decomposition rate at 90% or higher. This result indicates that by fusing the CBM of cellulosome with an auxiliary enzyme such as β-glucosidase, their behaviors can be coincided with each other during reaction, thus allowing the auxiliary enzyme itself to be recovered as in the case of cellulosome, which is revolutionary.

In order to check whether the recycling saccharification method using cellulosome and β-glucosidase fusing cellulose-binding module is also applicable to lignocellulose biomass, recycling saccharification reaction was caused using pretreated rice straws.

As pretreatment, ammonia immersion was performed. As ammonia-immersion treatment, to 10 g dried rice straws, 28% ammonia solution of 10 times the weight of the rice straws was added, and the mixture was then placed in an airtight container and left as it was at 60° C. for 7 days. Washing was then repeated using distilled water until neutrality was obtained. The straws were then drained and used as samples having undergone ammonia-immersion treatment.

In order to measure the total saccharides component and quantity of the rice straws having subjected to ammonia-immersion treatment, sulfuric acid hydrolytic degradation described in example was performed to prepare a hydrolysis solution, and high-performance liquid chromatography was performed.

Figure 8:
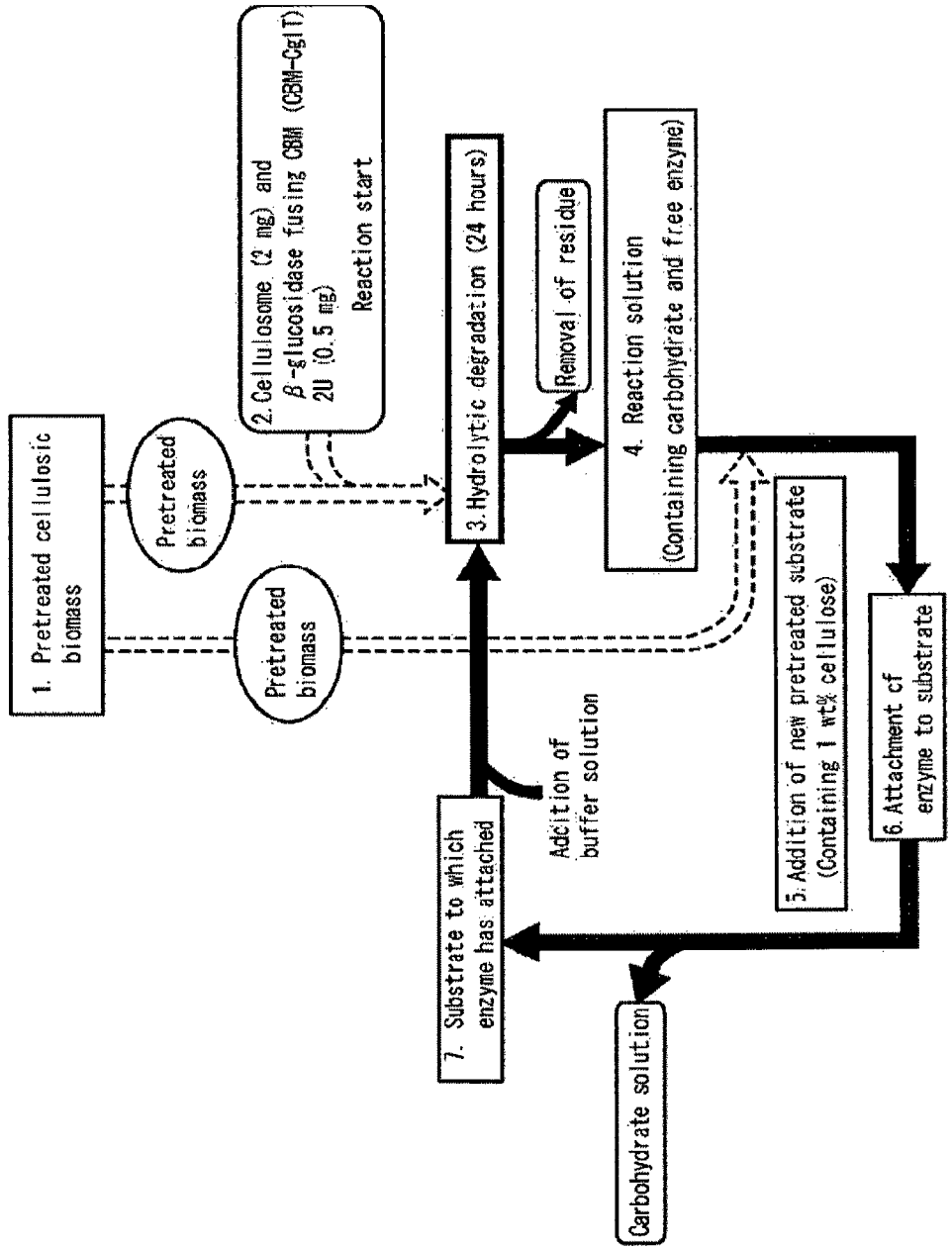
FIG. 8 illustrates a recycling saccharification method based on combined use of cellulosome and CBM-CgIT using lignocellulose biomass.

FIG. 8 illustrates the process of recycling saccharification using rice straws having undergone ammonia-immersion treatment. The cycle is basically the same as that in FIG. 4, except that the substrate is rice straws containing 1% cellulose and having undergone ammonia-immersion treatment. The process of removing the residue remaining after the hydrolytic degradation from the reaction system was followed strictly. By removing the residue from the reaction system, the number of times of recycling can be increased.

Figure 9:
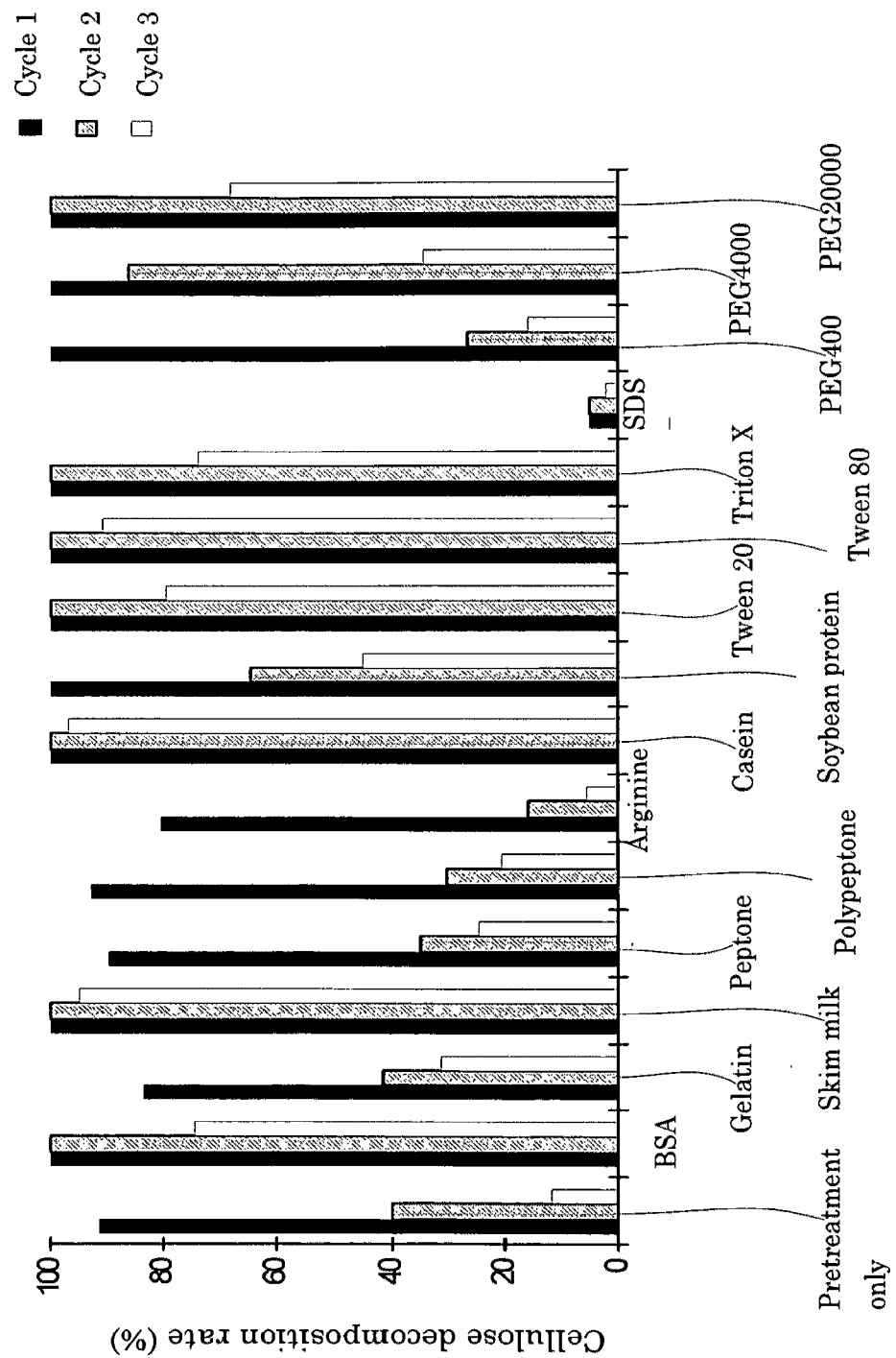
FIG. 9 is a chart comparing the cellulose decomposition rate by recycling saccharification of rice straws having undergone ammonia-immersion treatment and those having undergone ammonia-immersion treatment and then blocking treatment.

The amount of enzymes and reacting dose were the same as those in example 3. Namely, using 2 mg cellulosome and 0.5 mg CBM-CgIT (0.8 U), recycling saccharification reaction was started at 60° C. in a 100 mM acetic acid buffer solution containing 5 mM calcium chloride (pH 6.0). The results are shown in the lane marked as "pretreatment only" in FIG. 9. In the first round, the cellulose decomposition rate was higher than 90%. However, in the second and the subsequent rounds, the cellulose decomposition rate declined rapidly, with that in the third round as low as approximately 12%. The measurement of the amount of protein in the reaction solution confirmed that the amount of protein decreased rapidly after the start of the reaction, which means that nonspecific adsorption of enzyme by the rice straws having undergone ammonia immersion treatment was occurring.

Study was conducted to find whether it is possible to suppress nonspecific adsorption, thus continuing recycling saccharification, by coating the acid-insoluble region containing lignin of the lignocellulose biomass, which is considered to cause nonspecific adsorption.

Figure 10:
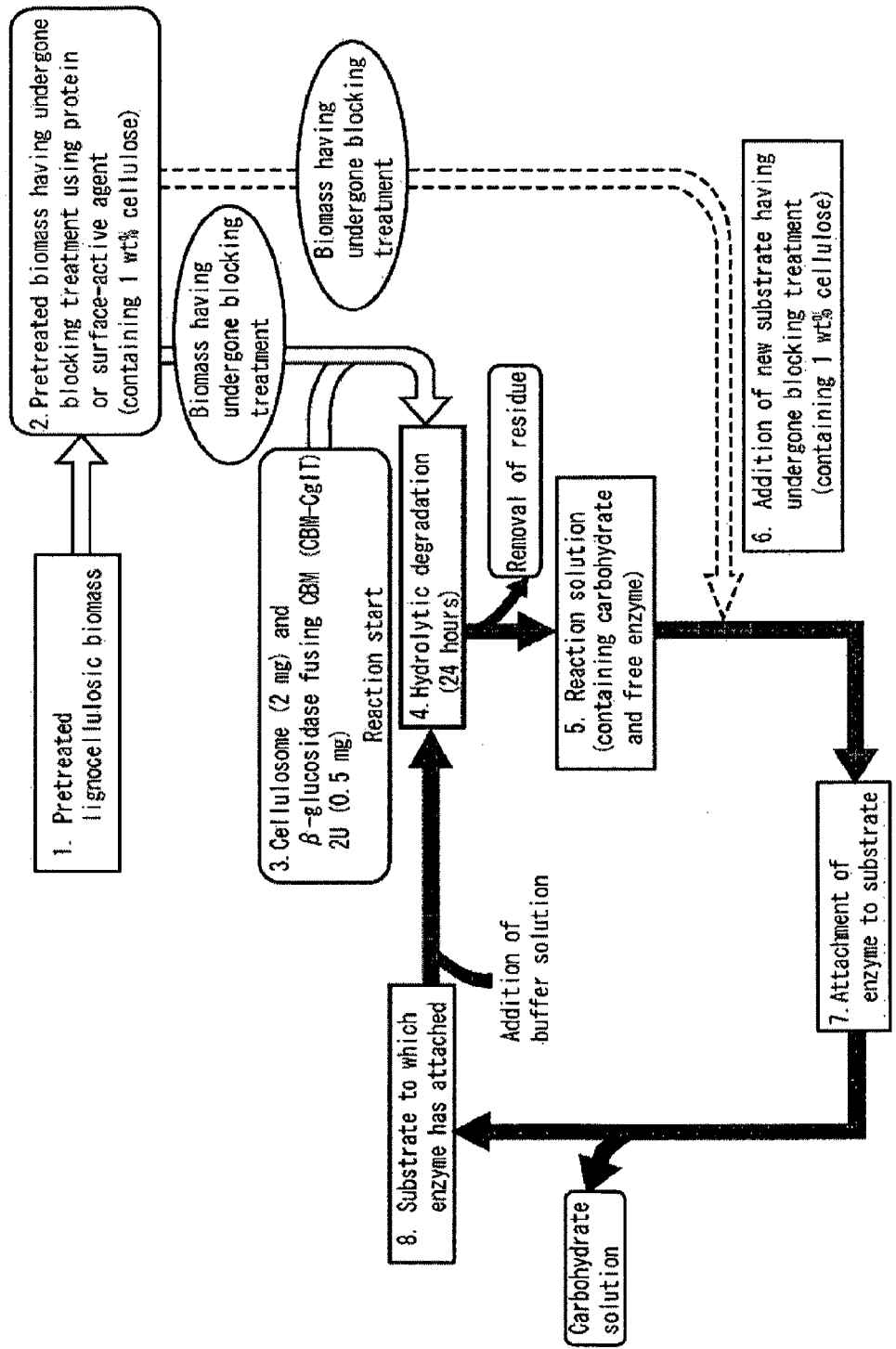
FIG. 10 is a chart illustrating the recycling saccharification process based on combined use of cellulosome and CBM-CgIT in the case where lignocellulosic biomass having undergone blocking treatment is used.

Rice straws having undergone ammonia-immersion treatment were subjected to blocking treatment using various proteins and surface-active agents prior to the reaction using cellulosome and CBM-CgIT. FIG. 10 illustrates this recycling process.

As blocking treatment, the pretreated biomass 1 g was immersed in a solution containing protein or surface-active agent of 0.2 wt % of the biomass at 4° C. or room temperature for 6 to 15 hours. Blocking reagents insoluble in distilled water were dissolved in a weak acid or alkaline solution for use. The cellulose content in the rice straws having undergone ammonia-immersion and blocking treatments to be added when this process was repeated was the same as that of the process without blocking treatment.

As coating agents, proteins such as bovine serum albumin (BSA) (Sigma-Aldrich Co.), gelatin (Wako Pure Chemical Industries, Ltd.), skim milk (Wako), and soybean protein (Wako); culture medium components such as peptone (Difco Labolatories) and polypeptone (Difco); amino acids such as arginine (Sigma-Aldrich); and various surface-active agents such as [Tween 20, 80] (Wako), Triton X (Wako), SDS (Wako); and polymers [PEG400-PEG20000 (Wako)] were used.

With bovine serum albumin (BSA), skim milk, and casein (proteins), non-ionic surface-active agents such as Tween 20 and Tween 80 (surface-active agents), and polyethylene glycol (PEG20000), high cellulose decomposition rate was maintained while recycling was performed repetitively. In particular, by coating the pretreated rice straws with skim milk, casein, or Tween 80, cellulose decomposition rate higher than 90% was maintained up to the third round.

Example 5

To check whether the saccharification based on the combined use of cellulosome and CBM-CgIT and saccharification adopting blocking treatment are effective for lignocellulose biomass other than rice straws, recycling saccharification tests were conducted using cedar pulp having undergone alkali pulping and waste office paper (washed with water), in addition to the rice straws having undergone ammonia-immersion treatment described above.

Cedar pulp was subjected to alkali pulping by adding a 23 wt % sodium hydroxide relative to the cedar pulp, and reaction was caused in a pressure-tight container at 170° C. for three hours. Then the pulp was washed thoroughly with water, and bleached with a chlorous acid solution (3.5 wt % relative to the pulp) at 60° C. for 30 minutes. Furthermore, the pulp was treated in a solution containing 4 wt % sodium hydroxide relative to the cedar pulp at 60° C. for 30 minutes, and washing was repeated until neutrality was obtained.

Waste office paper (recycled paper) was cut with a shredder, and then washed for an hour with distilled water for use.

In the case of blocking treatment using casein and Tween 80, each cellulose biomass was treated by the same method described in example 4 to use the biomass in the recycling saccharification reaction.

Figure 11:
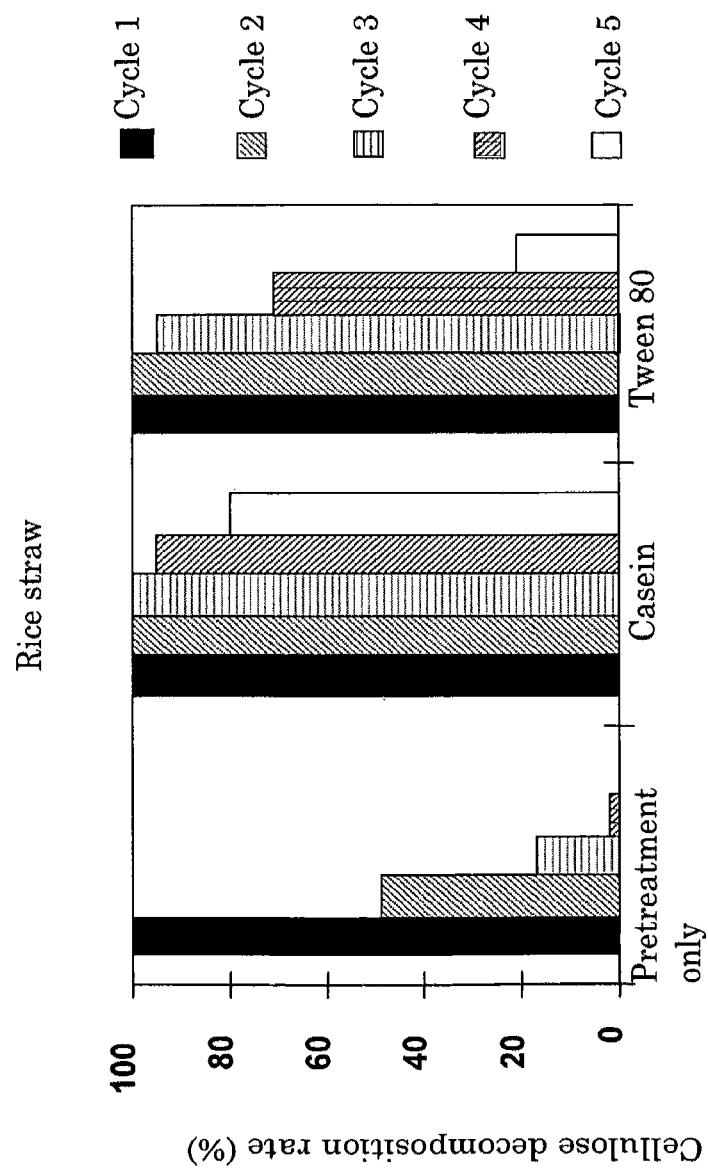
FIG. 11A is a chart comparing the cellulose decomposition rate by recycling saccharification using rice straws having undergone blocking treatment.
FIG. 11B is a chart comparing the cellulose decomposition rate by recycling saccharification using cedar pulp having undergone blocking treatment.
FIG. 11C is a chart comparing the cellulose decomposition rate by recycling saccharification using waste office paper having undergone blocking treatment.
Figure 11:
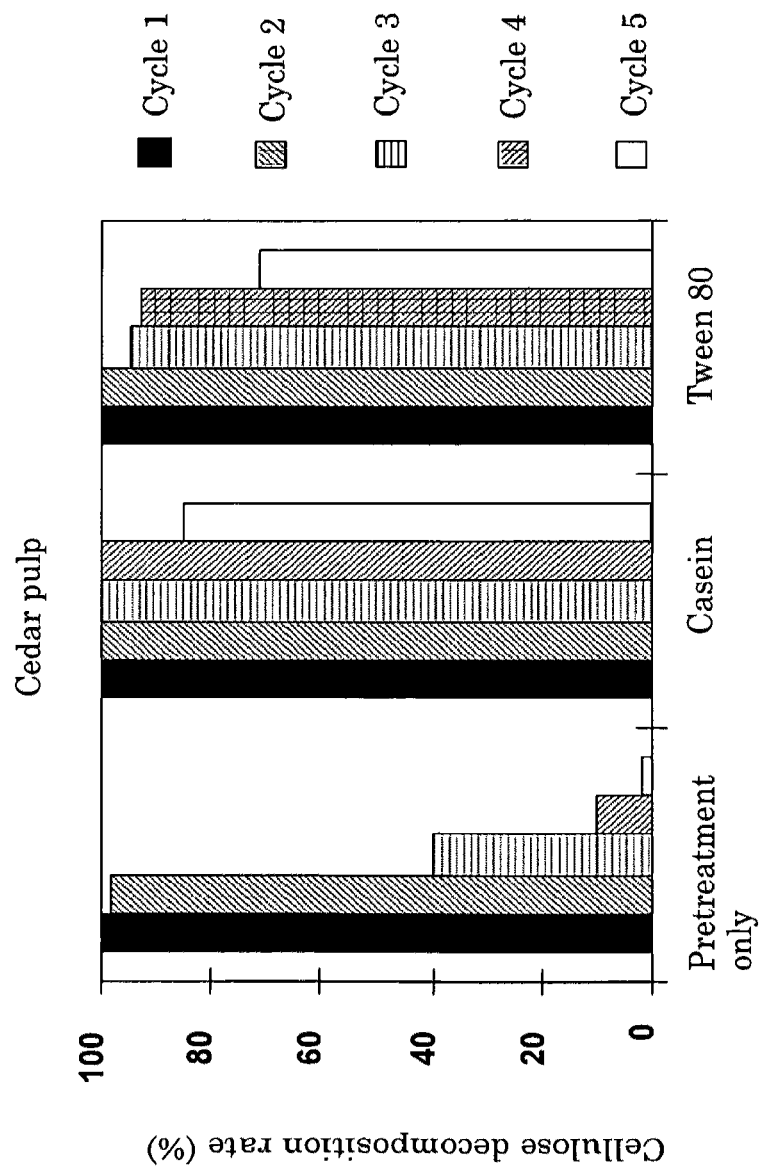
Figure 11:
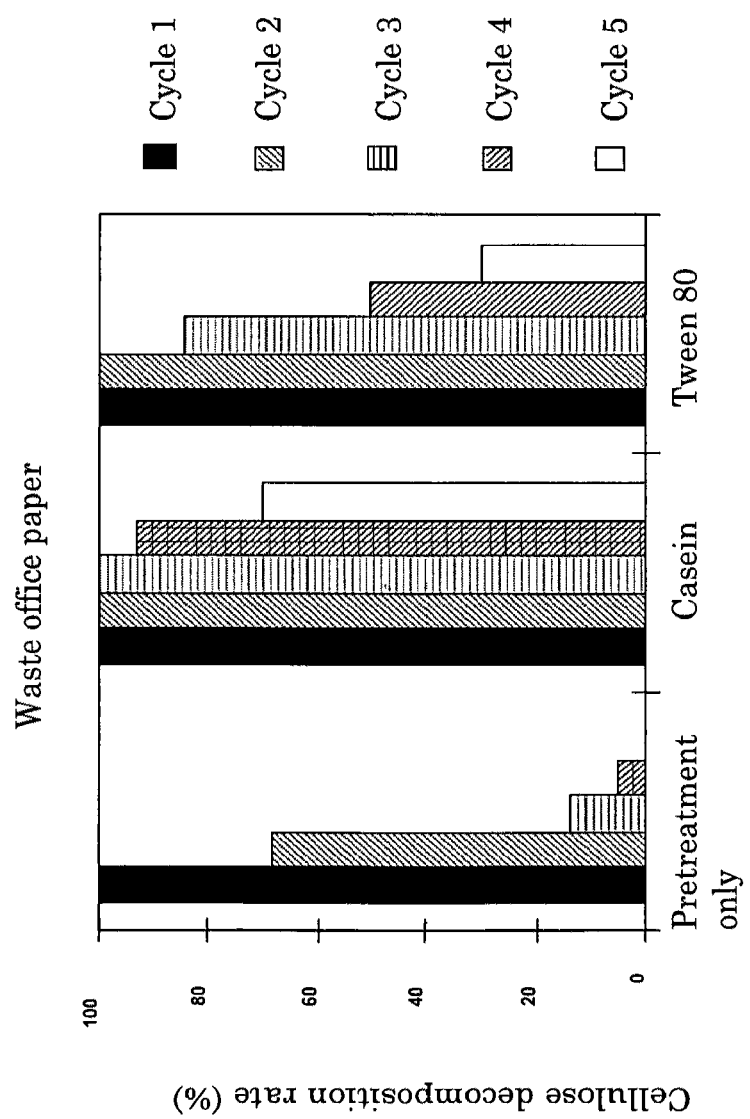

As with example 4, using 2 mg cellulosome and 0.5 mg CBM-CgIT (0.8 U), recycling saccharification reaction was started in a 100 mM acetic acid buffer solution containing 5 mM calcium chloride (pH 6.0) at 60° C. FIGS. 11A, 11B, and 11C show the results obtained.

As shown in FIGS. 11A to 11C, in the recycling saccharification reaction using cellulosome and CBM-CgIT in combination and with pretreatment only performed, rapid decrease in cellulose decomposition rate was observed from the second round with the rice straws having undergone ammonia-immersion treatment, and from the third round with the alkali pulped cedar pulp and office paper, followed by further decrease in the subsequent cycles. Meanwhile, cellulose decomposition rate as high as 70% was maintained even in the fourth cycle with the ammonia-immersed rice straws having undergone blocking treatment using casein or Tween 80, and even in the fifth cycle with the alkali pulped cedar pulp. These results exhibit that this recycling saccharification method is applicable to biomass other than rice straws.

Figure 12:
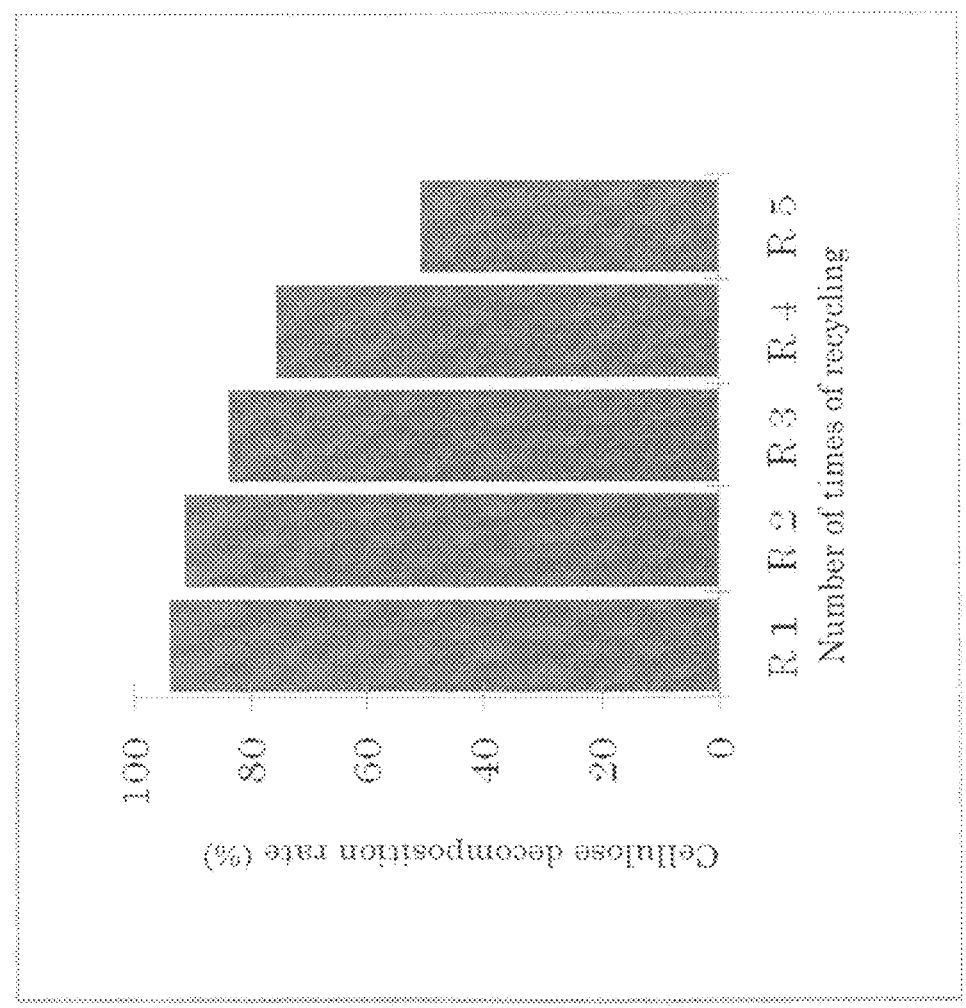
FIG. 12 is a chart illustrating cellulose decomposition rate of rice straws having undergone ammonia-immersion and blocking treatments using casein with residue left as it is.

When the cellulosic substrate is cellulosic biomass containing lignin and having undergone blocking treatment, it is also important to remove the residue remaining after hydrolytic degradation from the reaction system in order to increase the number of times of enzyme recycling. For the purpose of comparing the number of times of recycling allowed between the case in which the residue has not been removed and the one in which the residue has been removed from the reaction system, FIG. 12 exhibits the cellulose decomposition rate obtained when ammonia-immersed rice straws having undergone blocking treatment was used, with the reside left as it was.

When the residue was left in the reaction system, decrease in the saccharification efficiency was found with the increase in the number of times of recycling. The reason for the occurrence of this phenomenon is as follows: With the progress of reaction between the cellulosic biomass having undergone blocking treatment remaining in the reaction system and the enzymatic complex, nonspecific adsorption regions other than blocked regions begin to be exposed to combine the enzyme, and consequently the saccharification efficiency decreases if recycling is continued.

Example 6

Tests were conducted to check whether enzyme recycling reaction based on recycling saccharification process described above is applicable to fungus originated enzymes, which are not enzyme complex, unlike cellulosome, and have a function mechanism of decomposing lignocellulose as individual free enzymes. In the tests, the recycling saccharification capability of rice straws having undergone pretreatment only and those having undergone blocking treatment after the pretreatment was examined using commercially available fungus originated enzymes.

Figure 13:
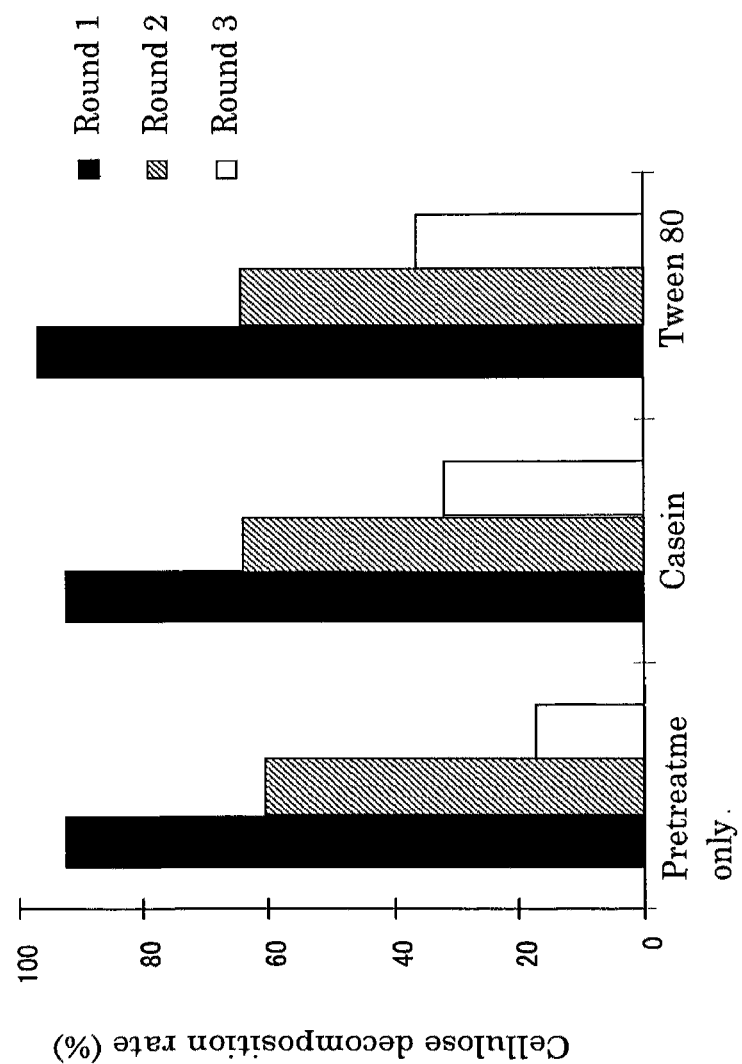
FIG. 13 is a chart illustrating the effect of recycling saccharification of rice straws using commercially available fungal cellulase and fungal β-glucosidase in combination.

*Trichoderma reesei*-derived cellulose (Sigma-Aldrich) and as β-glucosidase, the one derived from *Aspergillus niger* was used, which the β-glucosidase is same one used in the Example 1. Recycling saccharification reaction was started following the procedure shown in FIGS. 8 and 10 using 2 mg of the cellulose, 0.5 mg β-glucosidase, and a 100 mM acetic acid buffer solution (pH 5.0) at 50° C. The results are shown in FIG. 13.

With the ammonia-immersed rice straws, similar to the result of recycling saccharification using cellulosome and CBM-CgIT in combination, the cellulose decomposition rate of the first round was higher than 90%. However, the cellulose decomposition rate decreased rapidly in the second and subsequent rounds, which indicates that nonspecific adsorption to the enzyme by its substrate, namely the rice straws having undergone ammonia immersion treatment, was occurring.

Meanwhile, with the pretreated rice straws having undergone blocking treatment using casein and Tween 80, which had favorable effect on cellulosome recycling saccharification, the cellulose decomposition rate was found to decrease rapidly from the second round as in the case in which blocking treatment was not performed. This indicates that with fungus originated enzymes, not only nonspecific adsorption to the substrate inhibits enzyme recovery but also the enzymes essential to saccharification is discharged to outside the reaction system without being recovered. These results confirmed that the recycling saccharification method of the present invention is inadequate for diastatic enzymes functioning in a state where individual enzymes are free from each other such as fungus originated enzymes, on the other hand, it is essential to use enzymatic complex like cellulosome, in which required enzymes are combined as a set.

Example 7

Whether the same effect can be obtained if a small amount of various proteins, polyethylene glycol, or surface-active agent were added to cellulosome, instead of cellulosic biomass having undergone blocking treatment, was checked.

To enzyme solution of cellulosome and β-glucosidase (CBM-CgIT), casein or skim milk was added respectively in concentration of 0.2% (volume %). Using the enzyme solution containing the blocking agent, ammonia-immersed rice straws without blocking treatment, and cedar pulp having undergone alkali pulping treatment, enzyme recycling tests were conducted.

Figure 14:
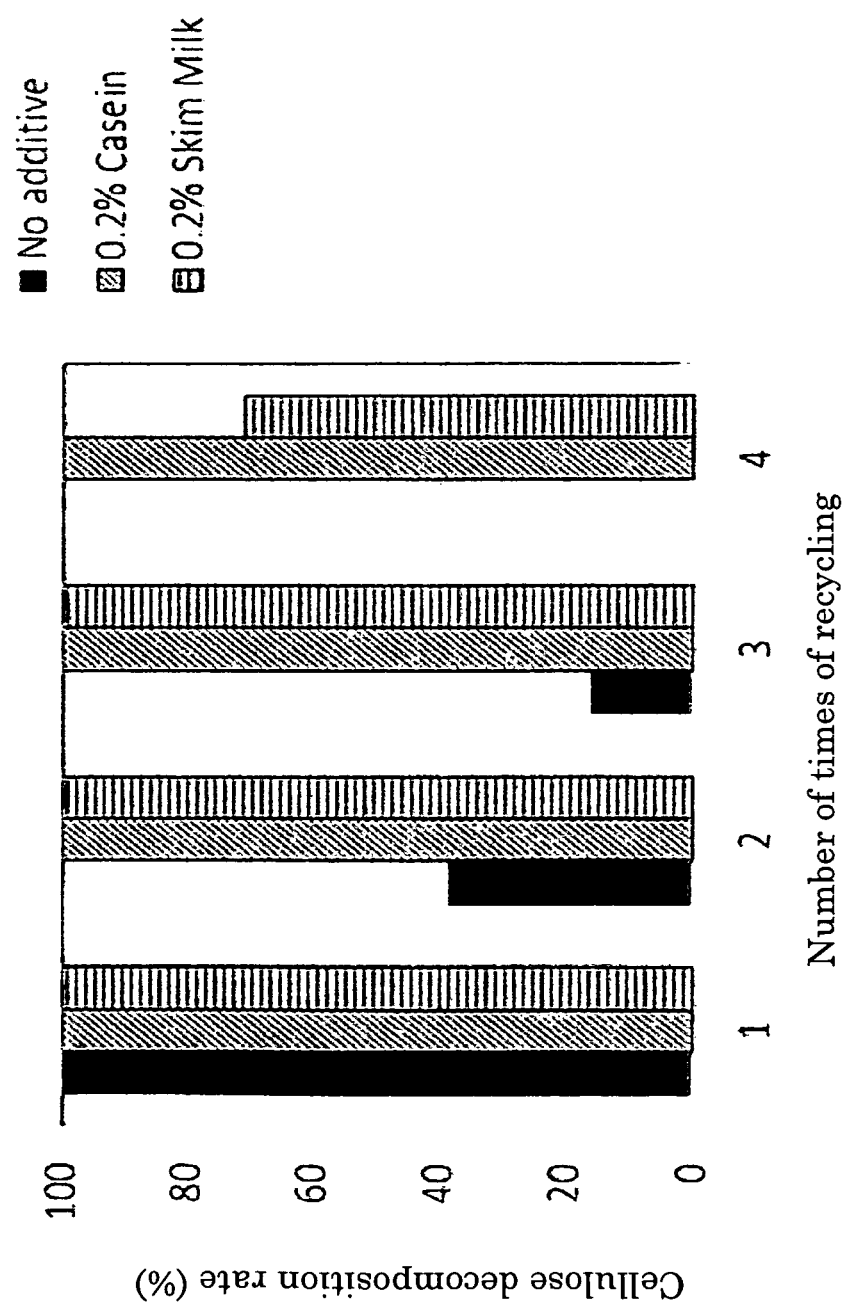
FIG. 14 is a chart illustrating the result of recycling saccharification performed with a blocking agent added to cellulosome and β-glucosidase (CBM-CgIT).

FIG. 14 shows the results. Unlike the enzyme solution to which casein or skim milk was not added, the number of times of recycling increased if casein or skim milk was added to the enzyme solution, and saccharification efficiency of over 90% was maintained at least up to the third round. The same effect as cellulosic biomass having undergone blocking treatment was thus obtained.

Example 8

When anaerobic bacteria-derived enzymes are used, a small amount of reducing agent such as dithiothreitol (DTT) or 2-mercaptoethanol may be added to cause enzyme reaction because the environment where the enzyme functions is also anaerobic. For cellulosome also, dithiothreitol of approximately 5 to 10 mM has been added to the reaction solution since long time ago (Appl. Environ. Microbiol 43:1125-1132). Therefore, 10 mM of DTT was added to the enzyme solution containing the blocking agent described above to check whether saccharification efficiency increasing effect can be obtained.

Figure 15:
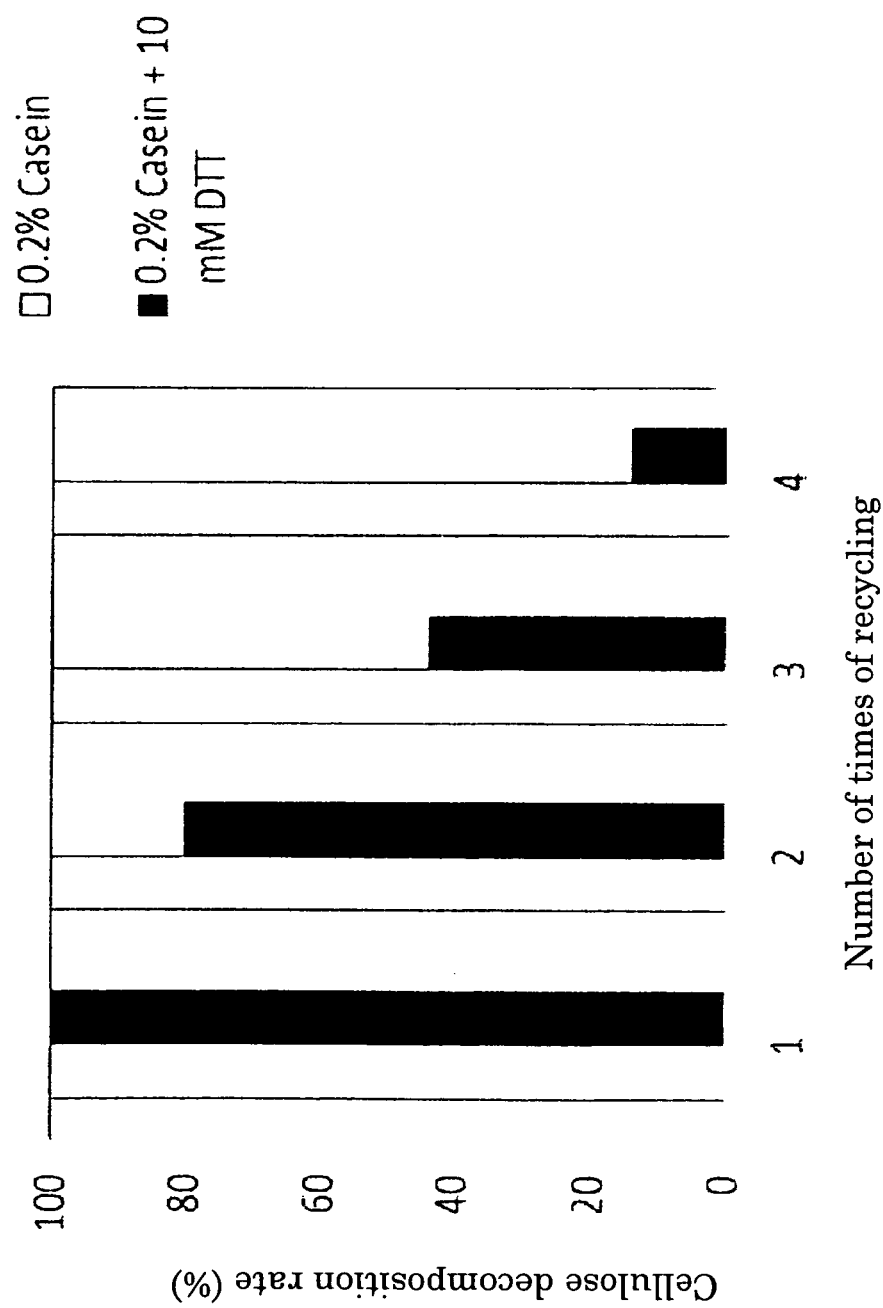
FIG. 15 is a chart illustrating the result of recycling saccharification containing DTT in the cellulosome enzyme reaction system.

FIG. 15 shows the results obtained. Every time recycling was repeated, the saccharification efficiency decreased, and by the third reuse, the saccharification efficiency decreased by more than 50%.

When 2-mercaptoethanol, cysteine, or ascorbic acid, which have reducing effect, was added also, saccharification efficiency decreased in the second and the third round. In recycling the above enzymes, it is therefore essential to remove chemical substances having reducing effect such as DTT.

What is claimed is:

1. A method for recycling an enzyme, comprising:
step A: adding a first substrate and a cellulosic substrate to an enzyme having a module that is combinable with cellulose to obtain and obtaining an enzyme reaction liquid that contains an enzyme combination formed by combining the enzyme with the cellulosic substrate;
step B: separating the enzyme combination from the enzyme reaction liquid;
step C: adding a substrate, a cellulosic substrate or both of the substrate and the cellulosic substrate to the enzyme combination; and
repeating the steps B and C using the enzyme combination in an enzyme reaction,
wherein the module is a carbohydrate binding module.

2. The method for recycling an enzyme as set forth in claim 1, wherein the substrate in the step A is an enzyme specific substrate.

3. A method for recycling enzymes, comprising:
step A: adding a first substrate and a cellulosic substrate to enzymes respectively having a module that is combinable with cellulose to obtain an enzyme reaction liquid that contains an enzyme combination formed by combining the enzymes with the cellulosic substrate;
step B: separating the enzyme combination from the enzyme reaction liquid;
step C: adding a substrate, a cellulosic substrate or both of the substrate and the cellulosic substrate to the enzyme combination; and
repeating the steps B and C using the enzyme combination in an enzyme reaction,
wherein the enzymes respectively include a cellulolytic enzyme having a carbohydrate binding module and β-glucosidase having a carbohydrate binding module.

4. The method for recycling enzymes as set forth in claim 3, wherein the cellulolytic enzyme is cellulosome.

5. The method for recycling enzymes as set forth in claim 4, wherein the β-glucosidase is a chimeric β-glucosidase having an amino-acid sequence of β-glucosidase derived from thermophilic bacteria and an amino-acid sequence of a carbohydrate binding module derived from cellulosome generated by *Clostridium*.

6. The method for recycling an enzyme as set forth in claim 1, wherein the cellulosic substrate is a cellulosic biomass containing lignin treated with at least one type of compound selected from a group consisting of protein, polyethylene glycol and surface active agent.

7. The method for recycling an enzyme as set forth in claim 1, wherein a residue other than the enzyme combination is removed from the enzyme reaction liquid containing enzymes in the step A or in the step C before the cellulosic substrate is added.

8. The method for recycling an enzyme as set forth in claim 6, wherein a residue other than the enzyme combination is removed from the enzyme reaction liquid containing enzymes in the step A or the step C before the cellulosic substrate is added.

9. The method for recycling an enzyme as set forth in claim 1, wherein, in the step A or the step C, the enzyme reaction liquid containing at least one type of compound selected from a group consisting of protein, polyethylene glycol, and surface active agent.

10. The method for recycling an enzyme as set forth in claim 7, wherein, in the step A or the step C, the enzyme reaction liquid containing at least one type of compound selected from a group consisting of protein, polyethylene glycol, and surface active agent.

11. The method for recycling an enzyme as set forth in claim 1, wherein, in the step A or the step C, the substrate is added to the enzyme in the absence of a reducing agent.

12. The method for recycling an enzyme as set forth in claim 6, wherein, in the step A or the step C, the substrate is added to the enzyme in the absence of a reducing agent.

13. The method for recycling an enzyme as set forth in claim 7, wherein, in the step A or the step C, the substrate is added to the enzyme in the absence of a reducing agent.

14. The method for recycling an enzyme as set forth in claim 8, wherein, in the step A or the step C, the substrate is added to the enzyme in the absence of a reducing agent.

15. The method for recycling enzymes as set forth in claim 3, wherein the β-glucosidase is derived from at least one thermophilic bacteria selected from the group consisting of *Acidothermus, Caldicellulosiruptor, Clostridium, Geobacillus, Thermobifida, Thermoanaerobacter, Thermobispora, Thermodesulfovibrio, Thermomicrobium, Thermomonospora, Thermosipho, Thermotoga, Thermus, Tolumonas, Treponema, Aciduliprofundum, Caldivirga, Desulfurococcus, Picrophilus, Pyrobaculum, Pyrococcus, Staphylothermus, Sulfolobus, Thermococcus, Thermofilum, Thermoplasma, Thermoproteus,* and *Thermosphaera,* and/or a bacteria producing an enzyme belonging to at least one family selected from the group consisting of families 1, 3, 9, 30, and 116.

16. The method for recycling enzymes as set forth in claim 4, wherein the β-glucosidase is derived from at least one thermophilic bacteria selected from the group consisting of *Acidothermus, Caldicellulosiruptor, Clostridium, Geobacillus, Thermobifida, Thermoanaerobacter, Thermobispora, Thermodesulfovibrio, Thermomicrobium, Thermomonospora, Thermosipho, Thermotoga, Thermus, Tolumonas, Treponema, Aciduliprofundum, Caldivirga, Desulfurococcus, Picrophilus, Pyrobaculum, Pyrococcus, Staphylothermus, Sulfolobus, Thermococcus, Thermofilum, Thermoplasma, Thermoproteus,* and *Thermosphaera,* and/or a bacteria producing an enzyme belonging to at least one family selected from the group consisting of families 1, 3, 9, 30, and 116.

17. The method for recycling enzymes as set forth in claim 5, wherein the β-glucosidase is derived from at least one thermophilic bacteria selected from the group consisting of *Acidothermus, Caldicellulosiruptor, Clostridium, Geobacillus, Thermobifida, Thermoanaerobacter, Thermobispora, Thermodesulfovibrio, Thermomicrobium, Thermomonospora, Thermosipho, Thermotoga, Thermus, Tolumonas, Treponema, Aciduliprofundum, Caldivirga, Desulfurococcus, Picrophilus, Pyrobaculum, Pyrococcus, Staphylothermus, Sulfolobus, Thermococcus, Thermofilum, Thermoplasma, Thermoproteus,* and *Thermosphaera,* and/or a bacteria producing an enzyme belonging to at least one family selected from the group consisting of families 1, 3, 9, 30, and 116.

18. The method for recycling an enzyme as set forth in claim 1, wherein the enzyme is cellulosome.

\* \* \* \* \*

SEQUENCE LISTING

```
<160> NUMBER OF SEQ ID NOS: 14

<210> SEQ ID NO 1
<211> LENGTH: 237
<212> TYPE: PRT
<213> ORGANISM: Clostridium thermocellum

<400> SEQUENCE: 1

Ala Thr Pro Thr Lys Gly Ala Thr Pro Thr Asn Thr Ala Thr Pro Thr
1               5                   10                  15

Lys Ser Ala Thr Ala Thr Pro Thr Arg Pro Ser Val Pro Thr Asn Thr
            20                  25                  30

Pro Thr Asn Thr Pro Ala Asn Thr Pro Val Ser Gly Asn Leu Lys Val
        35                  40                  45

Glu Phe Tyr Asn Ser Asn Pro Ser Asp Thr Thr Asn Ser Ile Asn Pro
    50                  55                  60

Gln Phe Lys Val Thr Asn Thr Gly Ser Ser Ala Ile Asp Leu Ser Lys
65                  70                  75                  80

Leu Thr Leu Arg Tyr Tyr Tyr Thr Val Asp Gly Gln Lys Asp Gln Thr
                85                  90                  95

Phe Trp Cys Asp His Ala Ala Ile Ile Gly Ser Asn Gly Ser Tyr Asn
            100                 105                 110

Gly Ile Thr Ser Asn Val Lys Gly Thr Phe Val Lys Met Ser Ser Ser
        115                 120                 125

Thr Asn Asn Ala Asp Thr Tyr Leu Glu Ile Ser Phe Thr Gly Gly Thr
130                 135                 140

Leu Glu Pro Gly Ala His Val Gln Ile Gln Gly Arg Phe Ala Lys Asn
145                 150                 155                 160

Asp Trp Ser Asn Tyr Thr Gln Ser Asn Asp Tyr Ser Phe Lys Ser Ala
                165                 170                 175

Ser Gln Phe Val Glu Trp Asp Gln Val Thr Ala Tyr Leu Asn Gly Val
            180                 185                 190

Leu Val Trp Gly Lys Glu Pro Gly Gly Ser Val Val Pro Ser Thr Gln
        195                 200                 205

Pro Val Thr Thr Pro Pro Ala Thr Thr Lys Pro Pro Ala Thr Thr Lys
    210                 215                 220

Pro Pro Ala Thr Thr Ile Pro Pro Ser Asp Pro Asn
225                 230                 235
```

```
<210> SEQ ID NO 2
<211> LENGTH: 780
<212> TYPE: DNA
<213> ORGANISM: Clostridium thermocellum

<400> SEQUENCE: 2
ggatttgcag ataatgacct ggtagaacag aaggtatcat ttatagacgg tggtgttaac      60
gttggcaatg caacaccgac caagggagca acaccaacaa atacagctac gccgacaaaa     120
tcagctacgg ctacgcccac caggccatcg gtaccgacaa acacaccgac aaacacaccg     180
gcaaatacac cggtatcagg caatttgaag gttgaattct acaacagcaa tccttcagat     240
actactaact caatcaatcc tcagttcaag gttactaata ccggaagcag tgcaattgat     300
ttgtccaaac tcacattgag atattattat acagtagacg gacagaaaga tcagaccttc     360
tggtgtgacc atgctgcaat aatcggcagt aacggcagct acaacggaat tacttcaaat     420
gtaaaaggaa catttgtaaa aatgagttcc tcaacaaata acgcagacac ctaccttgaa     480
ataagcttta caggcggaac tcttgaaccg ggtgcacatg ttcagataca aggtagattt     540
gcaaagaatg actggagtaa ctatacacag tcaaatgact actcattcaa gtctgcttca     600
cagtttgttg aatgggatca ggtaacagca tacttgaacg tgttcttgt atggggtaaa      660 gaacccggtg gcagtgtagt accatcaaca cagcctgtaa caacaccacc tgcaacaaca     720
aaaccacctg caacaacaaa accacctgca acaacaatac gccgtcaga tgatccgaat      780

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
cgcggatccg gcaaaatttc caagagat                                         28

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
attgctcagc atcttcgata ccatcatc                                         28

<210> SEQ ID NO 5
<211> LENGTH: 1358
<212> TYPE: DNA
<213> ORGANISM: Thermoanaerobacter brockii

<400> SEQUENCE: 5
cgcggatccg gcaaaatttc caagagattt cgtttggggg acagccacat catcatacca      60
aatagaagga gcggtaaatg aagacggaag gaccccttcc atatgggaca catttcaaa      120 aacagaaggg aagacctata aaggcctac aggagatgta gcctgtgacc attaccaccg     180
ctataaagaa gatgtagaga tattaaagaa aataggagta aaagcttaca gattttcaat     240
tgcatggcca agaattttcc ctgaggaagg gaaatacaat ccaaaaggga tggacttta      300 caagaagtta atagatgaat tacagaaaag agatatagta ccagctgcaa caattttatca    360 ctgggattta ccccaatggg cttatgacaa aggaggaggc tggctaaata gggaaagtat     420
```

```
aaaatggtat gtagaatacg ccacgaaact atttgaagaa ttaggcgatg cgatacccct    480
atggataact cataatgagc catggtgttc ctcaatatta agctatggaa taggagaaca    540
tgcgccaggg cacaaaaact acagagaggc actaatagca gctcatcata tactactttc    600
ccatggagaa gcagtaaaag cctttagaga aatgaatata aaagggagta agattggtat    660
aacactaaac ttaacccctg catatccagc cagcgaaaaa gaagaagaca aattagcagc    720
ccaatatgct gacggatttg ctaacagatg gttttagat ccaatattca aaggcaatta     780
tccagaggat atgatggaat tatatagtaa aataattgga gaatttgact ttataaaaga    840
aggagattta gagactataa gtgttccgat agatttctt ggagtcaatt attatacaag     900
aagtattgta aaatatgatg aagattccat gctaaaggca gagaatgtgc cggggccagg    960
taagaggacg gagatgggat gggagataag cccagagtct ttgtatgacc tttaaaaag   1020
gctagataga gaatatacaa aactgccat gtatatcaca gagaatggag cagcatttaa    1080
agatgaagtg acagaggatg gacgagtaca cgacgatgaa agaatagaat acattaaaga   1140
gcacttaaaa gcagcagcaa aatttatagg agaaggaggt aacttaaaag gatatttcgt   1200
atggtcgctg atggacaatt ttgaatgggc ccatggatat tcaaaagat ttgggatagt    1260
ttatgtggat tatactacac aaaagagaat attaaaagac agtgcattat ggtataaaga   1320
ggtaatattg gatgatggta tcgaagatgc tgagcaat                           1358
```

<210> SEQ ID NO 6
<211> LENGTH: 450
<212> TYPE: PRT
<213> ORGANISM: Thermoanaerobacter brockii

<400> SEQUENCE: 6

Met Ile Lys Leu Ala Lys Phe Pro Arg Asp Phe Val Trp Gly Thr Ala
1               5                   10                  15

Thr Ser Ser Tyr Gln Ile Glu Gly Ala Val Asn Glu Asp Gly Arg Thr
            20                  25                  30

Pro Ser Ile Trp Asp Thr Phe Ser Lys Thr Glu Gly Lys Thr Tyr Lys
        35                  40                  45

Gly His Thr Gly Asp Val Ala Cys Asp His Tyr His Arg Tyr Lys Glu
    50                  55                  60

Asp Val Glu Ile Leu Lys Glu Ile Gly Val Lys Ala Tyr Arg Phe Ser
65                  70                  75                  80

Ile Ala Trp Pro Arg Ile Phe Pro Glu Glu Gly Lys Tyr Asn Pro Lys
                85                  90                  95

Gly Met Asp Phe Tyr Lys Lys Leu Ile Asp Glu Leu Gln Lys Arg Asp
            100                 105                 110

Ile Val Pro Ala Ala Thr Ile Tyr His Trp Asp Leu Pro Gln Trp Ala
        115                 120                 125

Tyr Asp Lys Gly Gly Gly Trp Leu Asn Arg Glu Ser Ile Lys Trp Tyr
    130                 135                 140

Val Glu Tyr Ala Thr Lys Leu Phe Glu Glu Leu Gly Asp Ala Ile Pro
145                 150                 155                 160

Leu Trp Ile Thr His Asn Glu Pro Trp Cys Ser Ser Ile Leu Ser Tyr
                165                 170                 175

Gly Ile Gly Glu His Ala Pro Gly His Lys Asn Tyr Arg Glu Ala Leu
            180                 185                 190

Ile Ala Ala His His Ile Leu Leu Ser His Gly Glu Ala Val Lys Ala
        195                 200                 205

```
Phe Arg Glu Met Asn Ile Lys Gly Ser Lys Ile Gly Ile Thr Leu Asn
    210                 215                 220

Leu Thr Pro Ala Tyr Pro Ala Ser Glu Lys Glu Asp Lys Leu Ala
225                 230                 235                 240

Ala Gln Tyr Ala Asp Gly Phe Ala Asn Arg Trp Phe Leu Asp Pro Ile
                245                 250                 255

Phe Lys Gly Asn Tyr Pro Glu Asp Met Met Glu Leu Tyr Ser Lys Ile
                260                 265                 270

Ile Gly Glu Phe Asp Phe Ile Lys Gly Asp Leu Glu Thr Ile Ser
                275                 280                 285

Val Pro Ile Asp Phe Leu Gly Val Asn Tyr Tyr Thr Arg Ser Ile Val
290                 295                 300

Lys Tyr Asp Glu Asp Ser Met Leu Lys Ala Glu Asn Val Pro Gly Pro
305                 310                 315                 320

Gly Lys Arg Thr Glu Met Gly Trp Glu Ile Ser Pro Glu Ser Leu Tyr
                325                 330                 335

Asp Leu Leu Lys Arg Leu Asp Arg Glu Tyr Thr Lys Leu Pro Met Tyr
                340                 345                 350

Ile Thr Glu Asn Gly Ala Ala Phe Lys Asp Glu Val Thr Glu Asp Gly
                355                 360                 365

Arg Val His Asp Asp Glu Arg Ile Glu Tyr Ile Lys Glu His Leu Lys
                370                 375                 380

Ala Ala Ala Lys Phe Ile Gly Glu Gly Gly Asn Leu Lys Gly Tyr Phe
385                 390                 395                 400

Val Trp Ser Leu Met Asp Asn Phe Glu Trp Ala His Gly Tyr Ser Lys
                405                 410                 415

Arg Phe Gly Ile Val Tyr Val Asp Tyr Thr Thr Gln Lys Arg Ile Leu
                420                 425                 430

Lys Asp Ser Ala Leu Trp Tyr Lys Glu Val Ile Leu Asp Asp Gly Ile
                435                 440                 445

Glu Asp
    450

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
cgcggatccg gttggcaatg caacaccg                                    28

<210> SEQ ID NO 8
<211> LENGTH: 44
<212> TYPE: DNA
<213> ORGANISM: Artificial Sequence
<220> FEATURE:
<223> OTHER INFORMATION: primer

<400> SEQUENCE: 8
acgaaatctc ttggaaattt tgcattcgga tcatctgacg gcgg                  44

<210> SEQ ID NO 9
<211> LENGTH: 45
<212> TYPE: DNA
<213> ORGANISM: Artificial Sequence
<220> FEATURE:
<223> OTHER INFORMATION: primer
```

<400> SEQUENCE: 9
ccgccgtcag atgatccgaa tgcaaaattt ccaagagatt tcgtt                45

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
cggtgttgca ttgccaacat cttcgatacc atcatc                          36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gatgatggta tcgaagatgt tggcaatgca acaccg                          36

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
attgctcagc attcggatca tctgacggcg gtat                            34

<210> SEQ ID NO 13
<211> LENGTH: 2078
<212> TYPE: DNA
<213> ORGANISM: Artifical Sequence
<220> FEATURE:
<223> OTHER INFORMATION: chimera of CBM and CglTF

<400> SEQUENCE: 13
ccgcctcgag gttggcaatg caacaccgac caagggagca acaccaacaa atacagctac    60
gccgacaaaa tcagctacgg ctacgcccac caggccatcg gtaccgacaa acacaccgac   120
aaacacaccg gcaaatacac cggtatcagg caatttgaag gttgaattct acaacagcaa   180
tccttcagat actactaact caatcaatcc tcagttcaag gttactaata ccggaagcag   240
tgcaattgat ttgtccaaac tcacattgag atattattat acagtagacg gacagaaaga   300
tcagaccttc tggtgtgacc atgctgcaat aatcggcagt aacggcagct acaacggaat   360
tacttcaaat gtaaaaggaa catttgtaaa aatgagttcc tcaacaaata cgcagacac   420 ctaccttgaa ataagcttta caggcggaac tcttgaaccg ggtgcacatg ttcagataca   480
aggtagattt gcaagaatg actggagtaa ctatacacag tcaaatgact actcattcaa   540
gtctgcttca cagtttgttg aatgggatca ggtaacagca tacttgaacg gtgttcttgt   600
atggggtaaa gaacccggtg gcagtgtagt accatcaaca cagcctgtaa caacaccacc   660
tgcaacaaca aaaccacctg caacaacaaa accacctgca acaacaatac cgccgtcaga   720
tgatccgaat gcaaaatttc caagagattt cgtttggggg acagccacat catcatacca   780
aatagaagga gcggtaaatg aagacggaag gacccctttcc atatgggaca cattttcaaa   840
aacagaaggg aagacctata aaggccatac aggagatgta gcctgtgacc attaccaccg   900

```
ctataaagaa gatgtagaga tattaaaaga aataggagta aaagcttaca gattttcaat    960
tgcatggcca agaatttttcc ctgaggaagg gaaatacaat ccaaaaggga tggactttta   1020
caagaagtta atagatgaat tacagaaaag agatatagta ccagctgcaa caatttatca   1080
ctgggattta ccccaatggg cttatgacaa aggaggaggc tggctaaata gggaaagtat   1140
aaaatggtat gtagaatacg ccacgaaact atttgaagaa ttaggcgatg cgataccct    1200 atggataact cataatgagc catggtgttc ctcaatatta agctatggaa taggagaaca   1260
tgcgccaggg cacaaaaact acagagaggc actaatagca gctcatcata tactactttc   1320
ccatggagaa gcagtaaaag cctttagaga aatgaatata aagggagta agattggtat    1380 aacactaaac ttaacccctg catatccagc cagcgaaaaa gaagaagaca aattagcagc   1440
ccaatatgct gacggatttg ctaacagatg gttttttagat ccaatattca aaggcaatta  1500
tccagaggat atgatggaat tatatagtaa aataattgga gaattttgact ttataaaaga  1560 aggagattta gagactataa gtgttccgat agattttctt ggagtcaatt attatacaag   1620
aagtattgta aaatatgatg aagattccat gctaaaggca gagaatgtgc cggggccagg   1680
taagaggacg gagatgggat gggagataag cccagagtct ttgtatgacc tttttaaaaag  1740 gctagataga gaatatacaa aactgcctat gtatatcaca gagaatggag cagcatttaa   1800
agatgaagtg acagaggatg gacgagtaca cgacgatgaa agaatagaat acattaaaga   1860
gcacttaaaa gcagcagcaa aatttatagg agaaggaggt aacttaaaag gatatttcgt   1920
atggtcgctg atggacaatt ttgaatgggc ccatggatat tcaaaaagat ttgggatagt   1980
ttatgtggat tatactacac aaaagagaat attaaaagac agtgcattat ggtataaaga   2040
ggtaatattg gatgatggta tcgaagatgc tgagcaat                          2078
```

<210> SEQ ID NO 14
<211> LENGTH: 2078
<212> TYPE: DNA
<213> ORGANISM: Artifical Sequence
<220> FEATURE:
<223> OTHER INFORMATION: chimera of CBM and CglTF

<400> SEQUENCE: 14

```
cgcggatccg gcaaaatttc caagagattt cgtttggggg acagccacat catcatacca     60
aatagaagga gcggtaaatg aagacggaag gacccccttcc atatgggaca catttttcaaa   120 aacagaaggg aagacctata aaggccatac aggagatgta gcctgtgacc attaccaccg    180
ctataaagaa gatgtagaga tattaaaaga aataggagta aaagcttaca gattttcaat    240
tgcatggcca agaatttttcc ctgaggaagg gaaatacaat ccaaaaggga tggactttta   300
caagaagtta atagatgaat tacagaaaag agatatagta ccagctgcaa caatttatca    360
ctgggattta ccccaatggg cttatgacaa aggaggaggc tggctaaata gggaaagtat    420
aaaatggtat gtagaatacg ccacgaaact atttgaagaa ttaggcgatg cgataccct     480 atggataact cataatgagc catggtgttc ctcaatatta agctatggaa taggagaaca    540
tgcgccaggg cacaaaaact acagagaggc actaatagca gctcatcata tactactttc    600
ccatggagaa gcagtaaaag cctttagaga aatgaatata aagggagta agattggtat     660 aacactaaac ttaacccctg catatccagc cagcgaaaaa gaagaagaca aattagcagc    720
ccaatatgct gacggatttg ctaacagatg gttttttagat ccaatattca aaggcaatta   780
tccagaggat atgatggaat tatatagtaa aataattgga gaattttgact ttataaaaga   840 aggagattta gagactataa gtgttccgat agattttctt ggagtcaatt attatacaag    900
```

```
aagtattgta aaatatgatg aagattccat gctaaaggca gagaatgtgc cggggccagg      960
taagaggacg gagatgggat gggagataag cccagagtct ttgtatgacc ttttaaaaag     1020
gctagataga gaatatacaa aactgcctat gtatatcaca gagaatggag cagcatttaa     1080
agatgaagtg acagaggatg gacgagtaca cgacgatgaa agaatagaat acattaaaga     1140
gcacttaaaa gcagcagcaa aatttatagg agaaggaggt aacttaaaag gatatttcgt     1200
atggtcgctg atggacaatt ttgaatgggc ccatggatat tcaaaaagat ttgggatagt     1260
ttatgtggat tatactacac aaaagagaat attaaaagac agtgcattat ggtataaaga     1320
ggtaatattg gatgatggta tcgaagatgt tggcaatgca acaccgacca agggagcaac     1380
accaacaaat acagctacgc cgacaaaatc agctacggct acgcccacca ggccatcggt     1440
accgacaaac acaccgacaa acacaccggc aaatacaccg gtatcaggca atttgaaggt     1500
tgaattctac aacagcaatc cttcagatac tactaactca atcaatcctc agttcaaggt     1560
tactaatacc ggaagcagtg caattgattt gtccaaactc acattgagat attattatac     1620
agtagacgga cagaaagatc agaccttctg gtgtgaccat gctgcaataa tcggcagtaa     1680
cggcagctac aacggaatta cttcaaatgt aaaaggaaca tttgtaaaaa tgagttcctc     1740
aacaaataac gcagacacct accttgaaat aagctttaca ggcggaactc ttgaaccggg     1800
tgcacatgtt cagatacaag gtagatttgc aaagaatgac tggagtaact atacacagtc     1860
aaatgactac tcattcaagt ctgcttcaca gtttgttgaa tgggatcagg taacagcata     1920
cttgaacggt gttcttgtat ggggtaaaga acccggtggc agtgtagtac catcaacaca     1980
gcctgtaaca acaccacctg caacaacaaa accacctgca acaacaaaac cacctgcaac     2040
aacaataccg ccgtcagatg atccgaatgc tgagcaat                             2078
```